US009168100B2

(12) United States Patent
Hanson et al.

(10) Patent No.: US 9,168,100 B2
(45) Date of Patent: Oct. 27, 2015

(54) METHODS AND INSTRUMENTS FOR SUBCHONDRAL TREATMENT OF OSTEOARTHRITIS IN A SMALL JOINT

(71) Applicant: ZIMMER KNEE CREATIONS, INC., Exton, PA (US)

(72) Inventors: Shaun B. Hanson, West Chester, PA (US); Christopher D. Mandeen, West Chester, PA (US); Jamie A. Carroll, Drexel Hill, PA (US); Guido Laporta, Dalton, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 291 days.

(21) Appl. No.: 13/649,415

(22) Filed: Oct. 11, 2012

(65) Prior Publication Data

US 2013/0090662 A1 Apr. 11, 2013

Related U.S. Application Data

(60) Provisional application No. 61/545,846, filed on Oct. 11, 2011.

(51) Int. Cl.
*A61B 19/00* (2006.01)
*A61B 17/17* (2006.01)
*A61B 17/88* (2006.01)

(52) U.S. Cl.
CPC ............. *A61B 19/00* (2013.01); *A61B 17/1739* (2013.01); *A61B 17/8805* (2013.01); *A61B 2017/1775* (2013.01)

(58) Field of Classification Search
CPC ............... A61B 17/17; A61B 17/1717; A61B 17/1739; A61B 2017/1775
USPC ............................................. 606/96–98, 104
See application file for complete search history.

(56) References Cited

U.S. PATENT DOCUMENTS 5,514,137 A 5/1996 Coutts
5,556,429 A 9/1996 Felt
5,755,809 A 5/1998 Cohen (Continued)

FOREIGN PATENT DOCUMENTS

WO 2009/158522 A1 12/2009
WO 2011/063257 A1 5/2011

(Continued)

OTHER PUBLICATIONS

Invitation to Pay Additional Fees and Partial Search Report mailed on Jan. 8, 2013 in corresponding International Application No. PCT/US2012/059711.

(Continued)

*Primary Examiner* — Anu Ramana
(74) *Attorney, Agent, or Firm* — Schwegman Lundberg & Woessner, P.A.

(57) ABSTRACT

Devices, instruments and associated methods for the subchondral treatment of osteoarthritis in small joints are provided. In addition, a method for treating joint pain in small joints is provided. These small joints may be ankle, elbow or wrist joints. The methods may target one of many different access points having trajectories with a common focal point at or near the small joint. The instruments may limit access to areas within or near the small joint by providing predefined entry paths that avoid damage to surrounding tissues.

5 Claims, 25 Drawing Sheets

40A
44
42
48
48
46

(56) References Cited

U.S. PATENT DOCUMENTS

| | | | | |
|---|---|---|---|---|
| 6,140,452 | A | 10/2000 | Felt | |
| 6,235,043 | B1 | 5/2001 | Reiley | |
| 6,241,734 | B1 | 6/2001 | Scribner | |
| 6,248,110 | B1 | 6/2001 | Reiley | |
| 6,306,177 | B1 | 10/2001 | Felt | |
| 6,395,007 | B1 | 5/2002 | Bhatnagar | |
| 6,564,083 | B2 | 5/2003 | Stevens | |
| 6,607,561 | B2 | 8/2003 | Brannon | |
| 6,613,054 | B2 | 9/2003 | Scribner | |
| 6,719,761 | B1 | 4/2004 | Reiley | |
| 6,746,451 | B2 | 6/2004 | Middleton | |
| 6,827,720 | B2 | 12/2004 | Leali | |
| 6,863,899 | B2 | 3/2005 | Koblish | |
| 6,887,246 | B2 | 5/2005 | Bhatnagar | |
| 7,153,307 | B2 | 12/2006 | Scribner | |
| 7,261,720 | B2 | 8/2007 | Stevens | |
| 7,708,742 | B2 | 5/2010 | Scribner | |
| 7,771,431 | B2 | 8/2010 | Scribner | |
| 7,811,290 | B2 | 10/2010 | Rabiner | |
| 8,062,364 | B1 | 11/2011 | Sharkey et al. | |
| 8,152,813 | B2 | 4/2012 | Osorio | |
| 8,168,692 | B2 | 5/2012 | Wenz | |
| 2003/0138473 | A1 | 7/2003 | Koblish | |
| 2005/0119219 | A1 | 6/2005 | Bellini | |
| 2006/0064164 | A1 | 3/2006 | Theien | |
| 2006/0142870 | A1* | 6/2006 | Robinson et al. | 623/21.18 |
| 2010/0076503 | A1 | 3/2010 | Beyar | |
| 2010/0160925 | A1 | 6/2010 | Heilala et al. | |
| 2010/0179549 | A1 | 7/2010 | Keller | |
| 2011/0125156 | A1 | 5/2011 | Sharkey et al. | |
| 2011/0125157 | A1 | 5/2011 | Sharkey et al. | |
| 2011/0125264 | A1 | 5/2011 | Bagga et al. | |
| 2011/0125265 | A1 | 5/2011 | Bagga et al. | |
| 2011/0125272 | A1 | 5/2011 | Bagga et al. | |

FOREIGN PATENT DOCUMENTS

| | | | |
|---|---|---|---|
| WO | 2011/063267 | A1 | 5/2011 |
| WO | 2011/063281 | A1 | 5/2011 |
| WO | WO-2013055891 | A1 | 4/2013 |

OTHER PUBLICATIONS

International Search Report and Written Opinion mailed Mar. 4, 2013 in corresponding International Application No. PCT/US2012/059711.

International Application Serial No. PCT/US2012/059711, International Preliminary Report on Patentability mailed Apr. 24, 2014, 11 pgs.

May 12, 2008 Riddle Memorial Hospital, Medial, PA 19063 Operative Report. Surgeon: Peter F Sharkey, M.D.; Right knee, medial tibial plateau; A cannulated bone biopsy needle was placed into the bone under fluoroscopic guidance; Implant used: Stryker Orthopedics Hydroset (Bone Substitute Material); Surgeon also expressed difficulty in injecting the bone substitute.

Oct. 27, 2008 SPU Operative Report. Surgeon: Steven B Cohen, M.D.; An Anterior Cruciate Ligament (ACL) portal-creation device was repurposed for this surgery; The tibial probe was placed on the medial femoral condyle, with the tunnel guide secured proximally on the thigh; The surgeon expressed difficulty in positioning and stabilizing the guide; A cannulated pin was placed through the tunnel guide and placed distally into the medial femoral condyle; No implant was injected into the bone.

Nov. 10, 2008 SPU Operative Report. Surgeon: Steven B Cohen, M.D.; Treatment of the central medial tibial plateau; A guide pin was inserted into the medial tibial plateau; An endo button drill bit was used to expand the drill hole; One cubic centimeter (cc) of cement was inserted into the bone; A second drill hole was made from below, and a second cc was inserted into the bone.

* cited by examiner

METHODS AND INSTRUMENTS FOR SUBCHONDRAL TREATMENT OF OSTEOARTHRITIS IN A SMALL JOINT

CROSS-REFERENCE TO RELATED APPLICATIONS

This application claims priority to U.S. Provisional No. 61/545,846 filed Oct. 11, 2011 and entitled "Methods and Instruments for Subchondral Treatment of Osteoarthritis in the Ankle Joint," the content of which is incorporated by reference in its entirety.

FIELD

The present disclosure relates to devices and instruments for the surgical treatment of osteoarthritis at or near a joint, and more particularly to devices, instruments and associated methods for the subchondral treatment of osteoarthritis in a small joint, such as an ankle, wrist, or elbow joint.

BACKGROUND

Human joints, in particular the knee, hip, shoulder, ankle, and spine, are susceptible to degeneration from disease, trauma, and long-term repetitive use that eventually lead to pain. Joint pain arising from osteoarthritis, for example, is the impetus for a wide majority of medical treatments and associated medical costs. The most popular theory arising from the medical community is that joint pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in joints such as the knee and ankle, has been found to correlate poorly with the incidence and magnitude of the pain. Because of this, surgeons and medical practitioners have struggled to deliver consistent, reliable pain relief to patients, especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, microfracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore normal joint function. Both non-surgical and surgical treatments are currently available for joint repair.

The technique of subchondrally treating joints affected by osteoarthritis (OA) to relieve the associated pain, as well as treat the underlying disease, has been previously described by applicants. This subchondral treatment involves the stabilization and/or stimulation of the subchondral space at the area of the joint damaged by osteoarthritis, while also preserving as much as possible the articular surface of the joint. This subchondral treatment may be applied to all joints of the human body, including smaller joints such as ankle, elbow, or wrist joints.

In some cases, the ease with which the subchondral treatment developed by applicants is administered depends in large part on the instrumentation that is available to effect the treatment. One of the setbacks of using currently available surgical access devices and insertion tools is the lack of ability to target a specific area of the bone to be treated in a fast, accurate, easy and controlled manner. Presently, in order to treat or repair a bone defect at a joint, the surgeon often has to take multiple steps using multiple surgical tools in order to access, locate, and treat the target defect site. Even so, the surgeon does not have a reliable instrument or system that would allow him to easily and quickly target an area such as the subchondral region of a joint, and either deliver to, or remove material from, that target region. In order to perform repeated or multiple procedures in the same defect location with the currently available tools, additional and unnecessary time in the operating room would be required, as well as an increased risk for complications since numerous instruments and maneuvers are at play.

In the particular case of an ankle joint, the key bone is called the talus, or astralagus, bone. This is a small bone that sits between the heel bone (calcaneus) and the two bones of the lower leg (tibia and fibula). The talus has an irregular, humped shape, similar to that of a turtle. The bones of the lower leg articulate on top and around the sides to form the ankle joint. Where the talus meets the bones of the foot, it forms the subtalar joint, which is important for walking on uneven ground. Thus, the talus is an important connector between the foot and the leg and body, helping to transfer weight and pressure forces across the ankle joint. It is also for this reason that the talus is susceptible to fracture and degradation from osteoarthritis.

Due to the uniquely curved shape of the talus, subchondral treatment of the ankle joint may be challenging. In particular, precise, controlled and repeatable targeting of the subchondral region of the talus bone may be particularly difficult due to the inherent natural topography (i.e., curvature) of the bone. Accordingly, it is desirable to provide instruments that allow fast, easy, and controllable surgical access to the target site, or the bone defect within these small joints, to be treated. Even more desirable are instruments that allow reliable, repeatable and precise targeting and navigation to the subchondral target area of these small joints, such as the ankle joint. Thus, what are needed are instruments for subchondral treatment of small joints that accommodate their anatomy, and allow for treatment with ease, repeatability and accuracy.

SUMMARY

The present disclosure provides devices, instruments and associated methods for the subchondral treatment of joint pain and osteoarthritis of joints, and more specifically to instruments that allow fast, easy, precise, controllable and repeatable access to the subchondral bone of a small joint having osteoarthritis. For example, the small joint may be an ankle, elbow or wrist joint. In particular, devices, instruments and associated methods for the subchondral treatment of osteoarthritis in small joints are provided. In addition, a method for treating joint pain in small joints is provided. These small joints may be ankle, elbow or wrist joints. The methods may target one of many different access points having trajectories intersecting at a common focal point at or near the small joint. The instruments may limit access to areas within or near the small joint by providing predefined entry paths that avoid damage to surrounding tissues.

In one embodiment, a method for treating joint pain is provided. The method comprises: identifying a subchondral defect in a subchondral region of a bone of a joint; providing a guide instrument having portals representing predefined trajectories for accessing an internal area of the bone, wherein at least one or more of the trajectory paths intersects at a focal point; selecting a portal of the guide instrument corresponding to the selected subchondral access path; and treating the subchondral defect, via the selected portal of the guide instrument, while preserving the articular surface of the bone. The subchondral defect may be a bone marrow lesion, bone marrow edema, or insufficiency fracture. The joint may be a small joint, such as for example an ankle joint, wrist joint, elbow joint, or even shoulder joint. Treatment of the subchondral defect may comprise injecting a bone hardening material in the bone, or implanting a reinforcing member that stabilizes the subchondral defect.

In another embodiment, a guide instrument for delivering an instrument to a subchondral region of a joint is provided. The guide instrument may comprise a guide frame comprising at least one opening for receiving a fixation element; a detachable alignment bar connectable to the guide frame; and a guide ring comprising a plurality of openings for receiving therethrough an instrument or tool to the subchondral region of the joint, wherein each opening provides a predefined trajectory path into the subchondral region, at least one or more of the trajectory paths intersecting at a focal point. The guide instrument may be configured for use with a small joint, such as for example an ankle joint.

In yet another embodiment, a guide instrument for delivering an instrument to a subchondral region of a joint is provided. The guide instrument may comprise a main body having a generally wedge shape with a first end extending into a first flange and a second end extending into a second flange, each of said first and second flanges having one or more openings for receiving an instrument for insertion into the subchondral region of the joint to be treated, and wherein the openings of the first flange are elongated slots. The guide instrument may be configured for use with a small joint, such as for example an ankle joint.

In still another embodiment, a guide instrument for accessing a subchondral region of a joint is provided. The guide instrument may comprise a main body having one or more predefined angled portals extending therethrough, a tab extending from the main body and having a through-hole for attachment to a stabilizer, and an alignment arm extending from the main body, the alignment arm being configured to allow fluoroscopic verification of the angulation of the guide instrument with respect to an anatomical landmark. The guide instrument may be configured for use with a small joint, such as for example an ankle joint.

In yet another embodiment, a foot stabilizer and guided access instrument is provided. The instrument comprises a platform having a fastening element for securing to a foot; a track extending from the platform; an attachment arm adjustably movable along the track; and a guided access component adjustably connected to the attachment arm, the access component including a main body having a rotatable hub from which extends an access portal for guiding an instrument to a location on or near the foot, and a visualization bar to align the guided access component to an anatomical marker of the foot.

In still yet another embodiment, a foot stabilizer and guided access instrument is provided. The instrument may comprise a platform having a fastening element for securing to a foot, and a guided access component adjustably connected to the fastening element, the access component including a rotatable bar from which extends a pair of grid panels, each grid panel comprising a plurality of access portals for guiding an instrument to a location on or near the foot, wherein the grid panels further include visualization markers to align the panels relative to the foot.

In even still another embodiment, an instrument for guided access to a subchondral area of a joint is provided. The instrument may comprise a probe. The probe may have a handle extending into a guide body and a bone rest, the guide body comprising a platform including one or more portals for guided access of an instrument into a joint and being detachable from the handle, the bone rest being configured to rest against a bone of the joint.

In still another embodiment, a foot stabilizer and guided access instrument is provided. The instrument comprises a platform connected to a boot for receiving a foot therein, the boot comprising a plurality of access portals for the insertion of an instrument therethrough, the instrument being formed of a material for visualization during magnetic resonance imaging. The instrument may be attached to other guided access instruments such as those described herein.

In yet another embodiment, a tibial attachment instrument is provided. The instrument comprises an elongate shaft extending at one end into a proximal end plate and at an opposite end into a distal end plate, each of said plates including one or more holes for receiving a fixation element, the distal end plate further including a notched tab for receiving a guided access component.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 13-15 illustrate different MRI templates of various trajectory paths and focal points for insertion of instruments or devices relative to a foot using another exemplary embodiment of a guide instrument of the present disclosure, in which FIG. 13 represents an axial perspective, FIG. 14 represents an oblique perspective, and FIG. 15 represents a lateral perspective.

FIGS. 41-44 illustrate exemplary methods of treating a subchondral defect of an ankle joint by targeting different access points, in which FIG. 41 shows treatment through the talus bone, FIG. 42 shows treatment through the calcaneous bone, and FIGS. 43 and 44 show treatment through the tibia bone.

DESCRIPTION OF THE EMBODIMENTS

Figure 1:
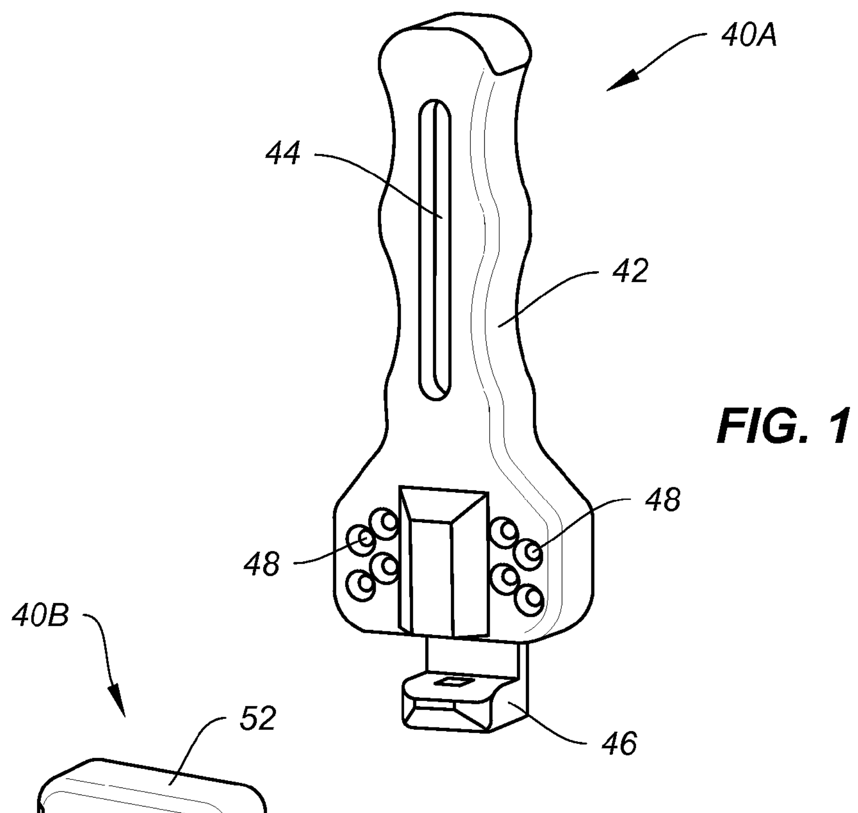
FIG. 1 is a perspective view of an exemplary embodiment of a guide frame of the present disclosure.

The present disclosure provides methodologies, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total joint replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for SCP™ for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

A number of treatment modalities, and associated devices, instruments and related methods of use for performing SUBCHONDROPLASTY™ are disclosed in the aforementioned publications. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In load-bearing joints, the implant may support compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by reference. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In general, the present disclosure provides embodiments related to instruments and associated methods for the surgical treatment of a small joint, and particularly to a bone defect at that small joint region. More specifically, the embodiments relate to instruments for navigating and positioning devices into an area sufficiently near a defect of the small joint. Even more specifically, the instruments and associated methods for use are suitable for the repair of the small joint, such as an ankle, elbow, wrist, or even shoulder joint. These instruments and devices may be used in a manner consistent with the subchondral procedures previously described.

In a healthy joint, the compressive load between the contact bones is properly distributed, thus keeping the contact stresses in the cartilage to a reasonably low level. As the cartilage starts to wear out or degenerate locally, the contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates joint pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, normal physiologic stress distribution can be achieved, and mechanical congruity restored, thereby resulting in healing of the inflammation and reduction or elimination of pain. The same type of pathology appears in non-load bearing joints such as the wrist, elbow or shoulder joints, so the treatment modalities described herein are equally applicable to osteoarthritic wrist, elbow or shoulder joints as well.

As previously mentioned, there is a need for surgical instruments that will facilitate the application of the methodologies described above at the target site, or the bone defect, to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area, and therefore require more precise defect location features. These instruments are also particularly suited to deliver bone substitute material, devices, implants, etc. without disrupting the joint surface. Accordingly, the present disclosure provides suitable instruments and associated methods for the surgical treatment of these bone defects, especially at the subchondral level near sclerotic bone.

As previously mentioned, there is a need for surgical instruments that will facilitate the application of the methodologies described above at the target site, or the bone defect, to be treated. Particularly desirable are instruments that allow for the application of the methodologies just described for small joints, such as the ankle joint. Accordingly, the present disclosure provides suitable instruments and devices, and associated methods, for the surgical treatment of these bone defects, especially at the subchondral level near sclerotic bone of these small joints.

In general, the present disclosure provides devices, instruments and associated methods for the subchondral treatment of osteoarthritis in small joints. For example, these small joints may be ankle, wrist, elbow, or even shoulder joints. Accordingly, embodiments of the present disclosure may be explained and illustrated with reference to treatment of a patient's ankle joint. It is, of course, understood that the concepts described herein apply equally to other small joints, such as the elbow, wrist or even shoulder joint.

Figure 2:
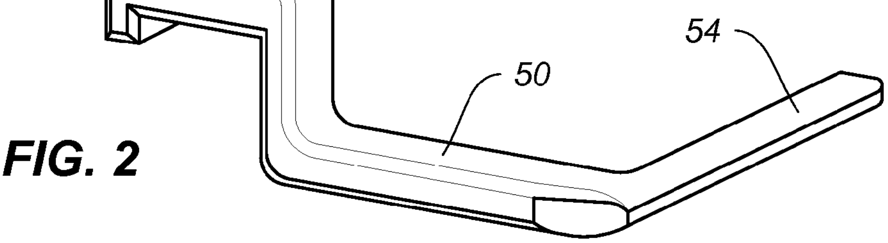
FIG. 2 is a perspective view of an exemplary embodiment of an alignment arm of the present disclosure.
Figure 3:
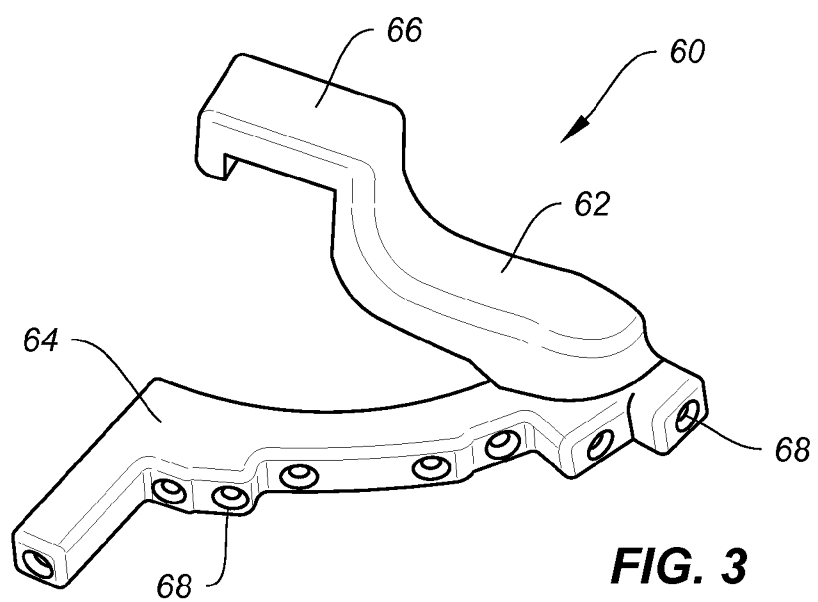
FIG. 3 is a perspective view of an exemplary embodiment of a reference guide ring of the present disclosure.
Figure 4:
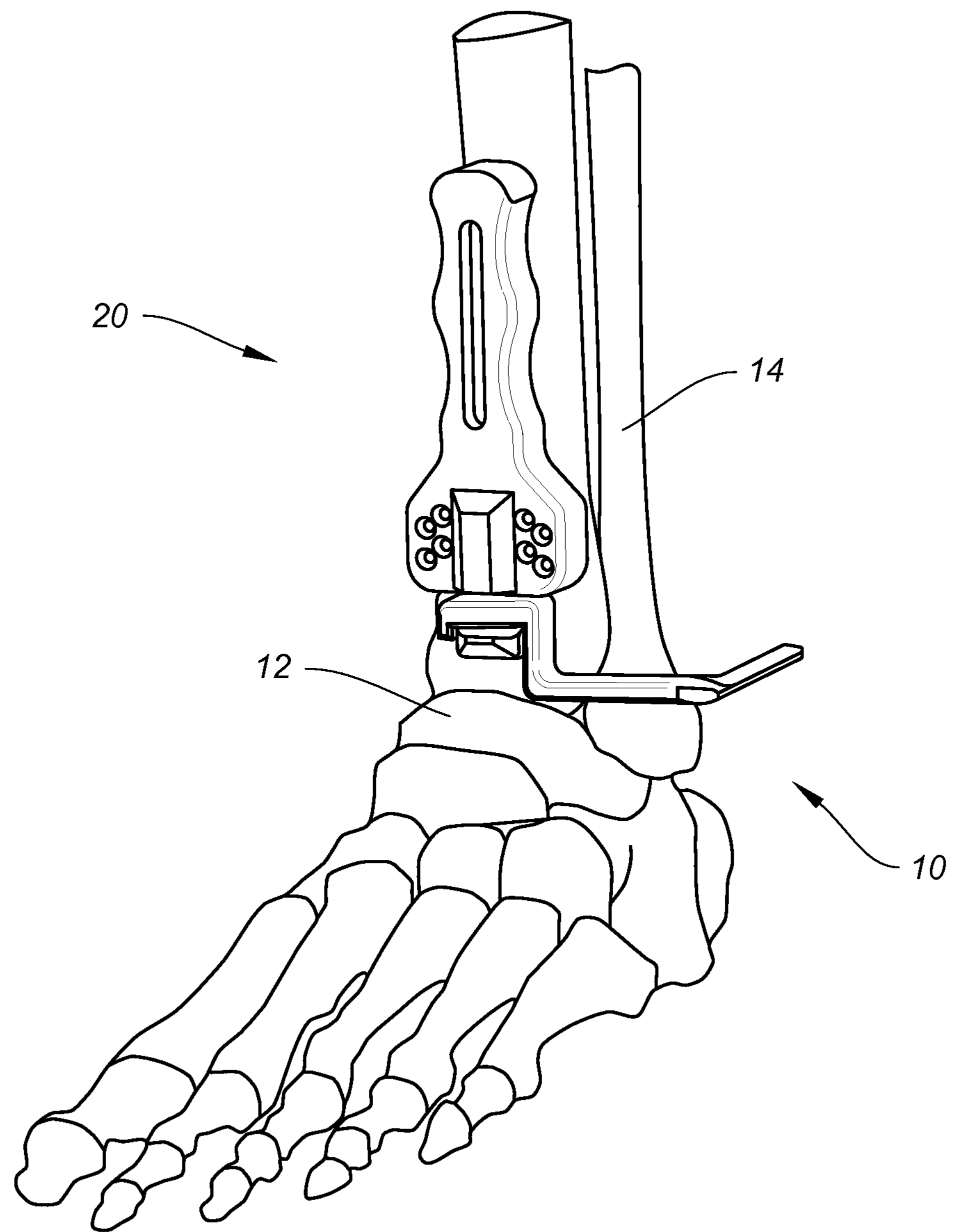
FIG. 4 shows an exemplary embodiment of a guide or navigation instrument of the present disclosure positioned relative to an ankle joint.

Turning now to the drawings, FIGS. 1 to 3 illustrate various components of a guide or navigation instrument 20, usable with the ankle joint 10 as shown in FIG. 4. FIG. 1 shows a guide frame 40A comprising a main body 42 having an elongate slot 44 and a notched tab 46 for receiving a detachable alignment bar 40B, as shown in FIG. 2. The main body 42 also comprises a plurality of openings 48 for the insertion of fixation devices to secure the guide frame 40A to a bone. The alignment bar 40B includes a main body 50 extending into a notched arm 52 that is configured to be received in the notched tab 46 of the guide frame 40A. The main body 50 also extends into a side arm 54, as shown.

Figure 5:
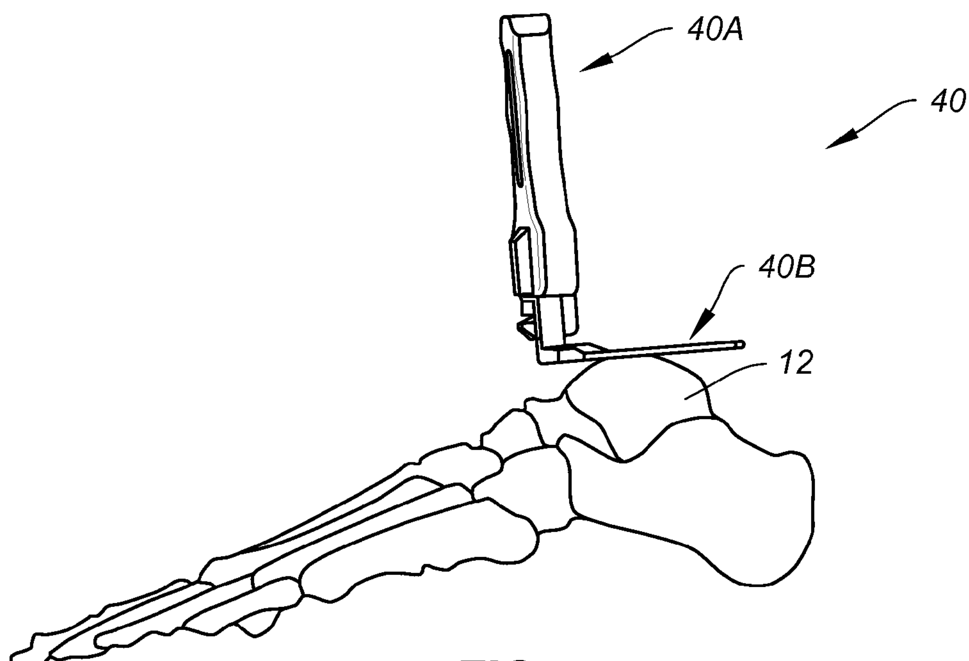
FIG. 5 shows a perspective side view of the guide instrument of FIG. 4 aligned to a talar bone.
Figure 6:
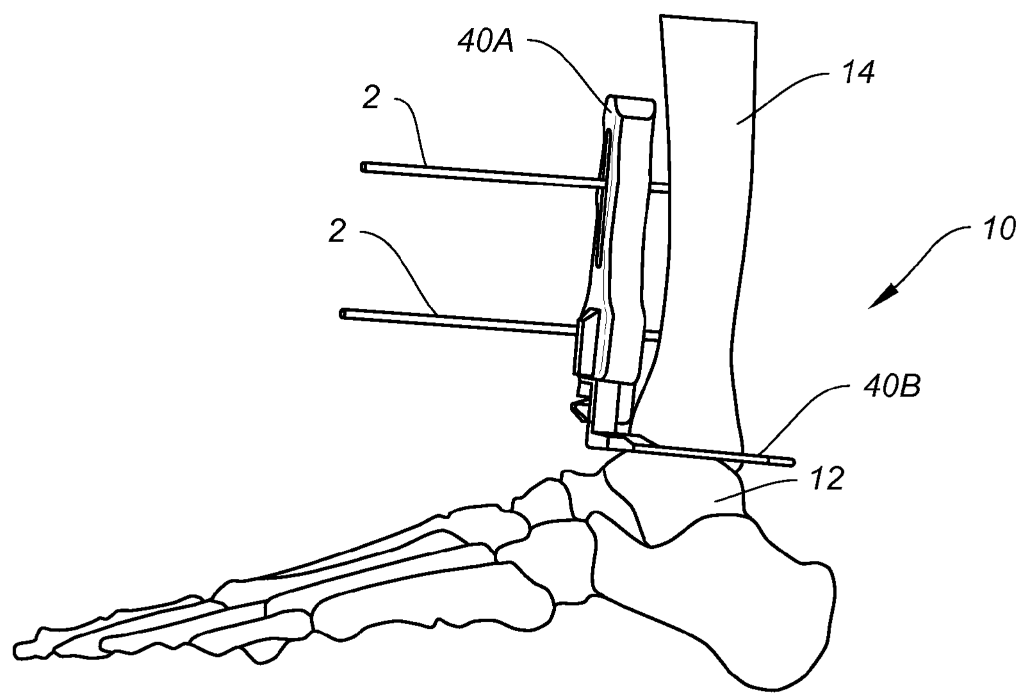
FIG. 6 shows the guide instrument of FIG. 5 fixed to the anterior portion of the tibia.

In use, the guide frame and bar 40A, 40B may be attached together to form a tibial fixation assembly 40 and placed relative to an ankle joint 10 to be treated, as illustrated in FIGS. 4 and 5. The fixation assembly 40 may be aligned to the dome of the talus 12, as shown, or any other desired anatomical landmark. Once properly positioned, the guide frame may be fixed to the tibia 14 with pins 2. These pins 2 may be placed through the elongate slot 44 of the main body 42 of the guide 40A, at any point along its length, or through one of the openings 48, as further shown in FIGS. 6 and 7.

Figure 7:
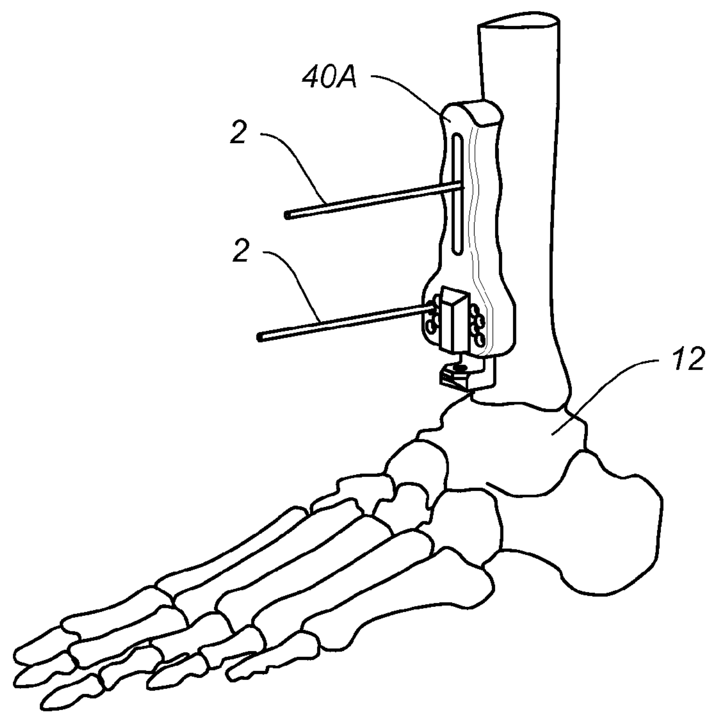
FIG. 7 shows the guide frame of FIG. 6 alone, attached to the tibia.
Figure 8:
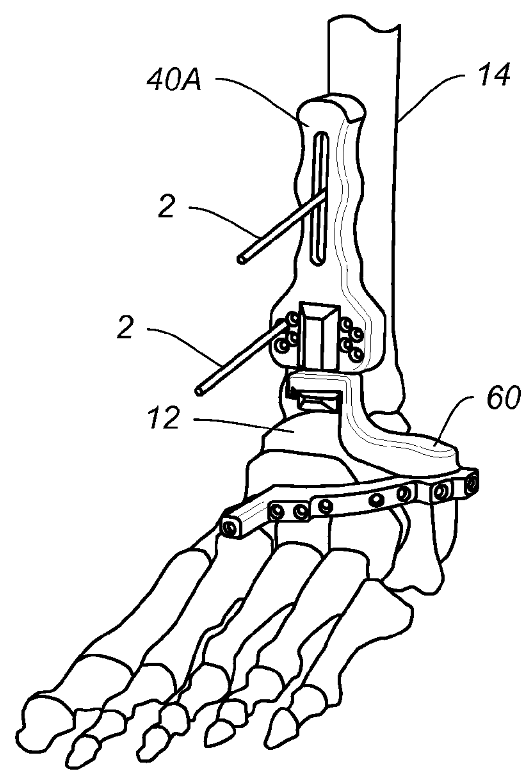
FIG. 8 shows the guide frame of FIG. 7 with the guide ring of FIG. 3.

After fixing the fixation assembly 40 to the anterior portion of the tibia 14, the detachable alignment bar 40B may be removed, leaving the guide frame 40A remaining and fixed to the tibial bone 14, as shown in FIG. 7. Next, a reference guide ring 60 (FIG. 3) may be placed onto the guide frame 40A, as shown in FIG. 8. The guide ring 60 may comprise a main body 62 from which extends a notched arm 66 for attachment to the notched tab 46 of the guide frame 40A. Attached to the main body 62 is a positioning arm 64 that contains a plurality of openings 68.

The openings 68 on the positioning arm provide entry points for an instrument or device into the ankle joint 10, and in particular to the subchondral region of the talus bone 12 of the ankle joint 10. These openings 68 may represent common entry points for a minimally invasive treatment of the talus 12. Of course, for any given plane or angle of insertion desired for entry into the talus 12, the present guide frame system 20 allows for adjustment or settings for the angle of approach based on the surgeon's preference. The openings 68 are each configured with a specific trajectory to allow the same length or depth pin to be inserted through a plurality of these openings 68 and target through a desired surgical entry focal point into the talus bone 12, allowing the ability to pinpoint any defect at different anatomical locations inside the talus 12. Surgical access to the talus 12 can be difficult and limited due to the surrounding complexity of tissues including critical nerves, tendons, ligaments, arteries, veins, and articulating joint surfaces. In order to avoid damage to these surrounding tissues, surgical treatment to the talus 12 is limited to access paths through a small number of focal areas. Thus, the trajectories though openings 68 in the device provide for access to many internal points in the talus 12 through a focal surgical access entry point at a location set to avoid damage to surrounding tissues.

A map of corresponding injection areas can be created by approaching the talus bone 12 through these multiple openings 68 provided on the guide ring 60, and in a minimally invasive manner. The map of these trajectories can correspond to a MRI or other anatomical template used in surgical planning to determine the specific trajectory needed to target the location of the lesion as seen in the MRI. These openings 68 may be sized and shape to allow the insertion of an instrument, device or both, in accordance with the treatment methods just described for treating a subchondral defect of the ankle joint 10. These openings 68 could, of course, also be configured to receive fixation pins 2 as shown.

Figure 9:
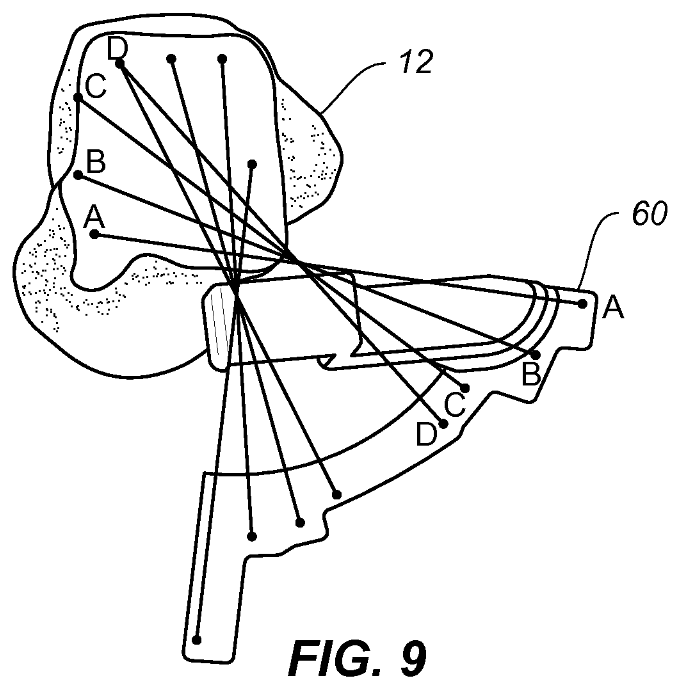
FIG. 9 shows various trajectory paths along the guide ring of FIG. 3.
Figure 10:
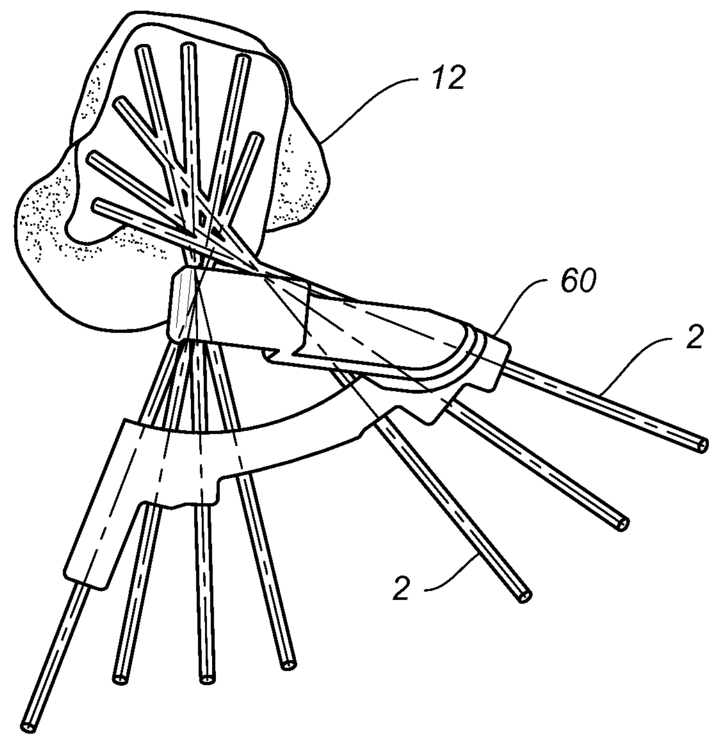
FIG. 10 shows pins inserted through the openings along the trajectory paths of FIG. 9 of the guide ring.
Figure 11:
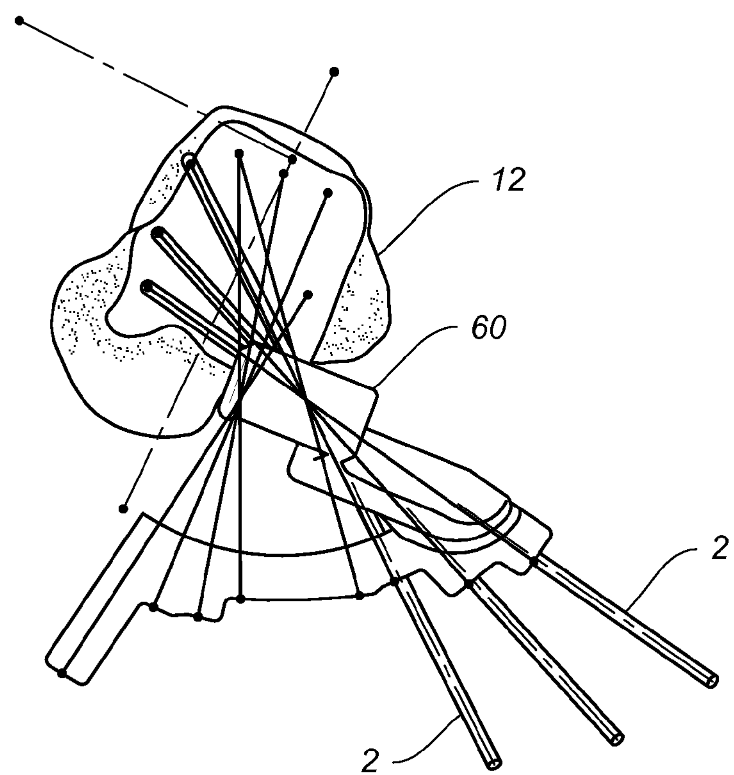
FIG. 11 shows a partial exposed view of the various trajectory paths and inserted pins of FIGS. 9 and 10 relative to a talus.
Figure 12:
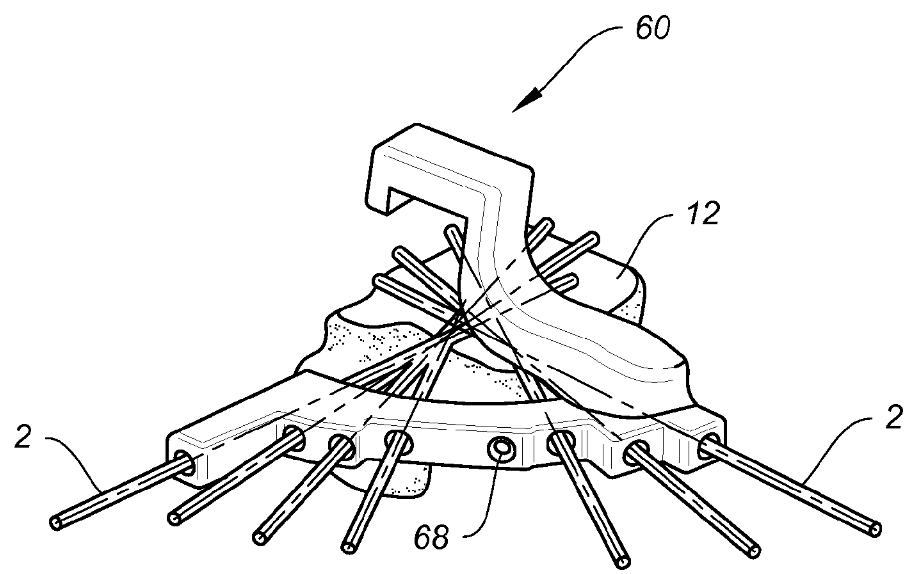
FIG. 12 shows a partial exposed view of the inserted pins and guide ring of FIG. 10 relative to a talus.

FIGS. 9-12 illustrate the concept previously describe regarding the multiple trajectories or access paths to the talus 12. For example, FIG. 9 shows various trajectory paths along the guide ring 60 via the openings 68 (e.g, lines A-A, B-B, C-C, and D-D all converge at a specific focal point, as shown). FIG. 10 shows fixation pins 2 inserted through the openings 68 along these trajectory paths relative to a talus 12. FIG. 11 shows fixation pins 2 inserted through select openings 68 of the guide ring 60 and extending along select trajectory paths, converging and diverging through a common focal entry point, relative to the talus 12. FIG. 12 shows a plurality of inserted pins 2 through openings 68 of the guide ring 60 relative to the talus 12. As FIGS. 9-12 illustrate, there are many possible trajectories for the pin 2 or pins 2 to reach different areas of the talus 12 to treat a subchondral defect in the manner previously described. Thus, the guide ring 60 is capable of directing a constant depth pin 2 or a plurality of pins 2 to specific locations that can be mapped on a template, if so desired.

Figure 13:
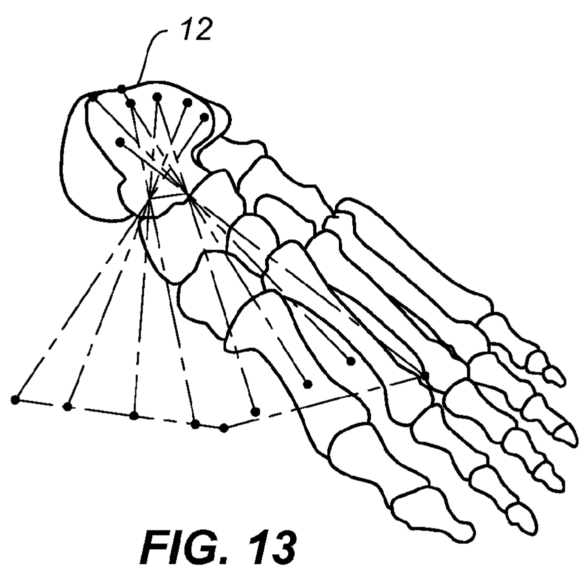
Figure 14:
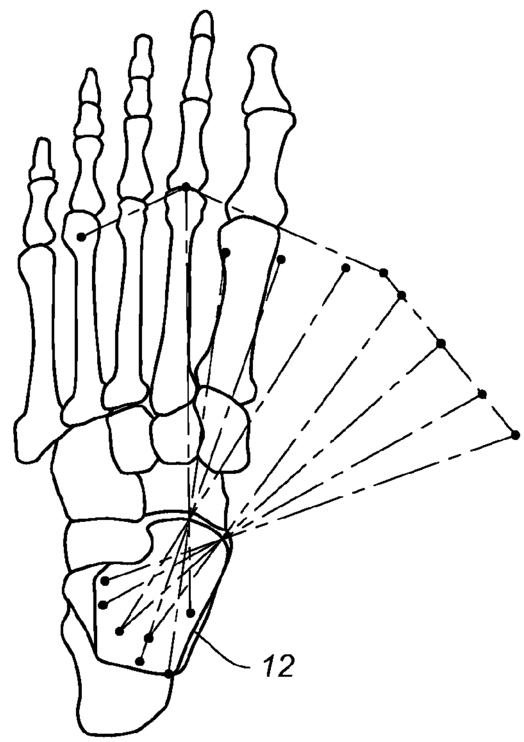
Figure 15:
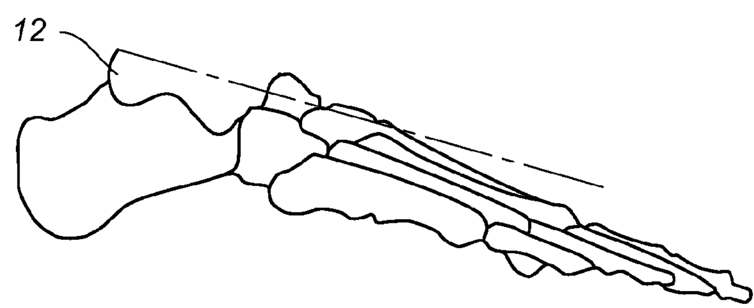
Figure 16:
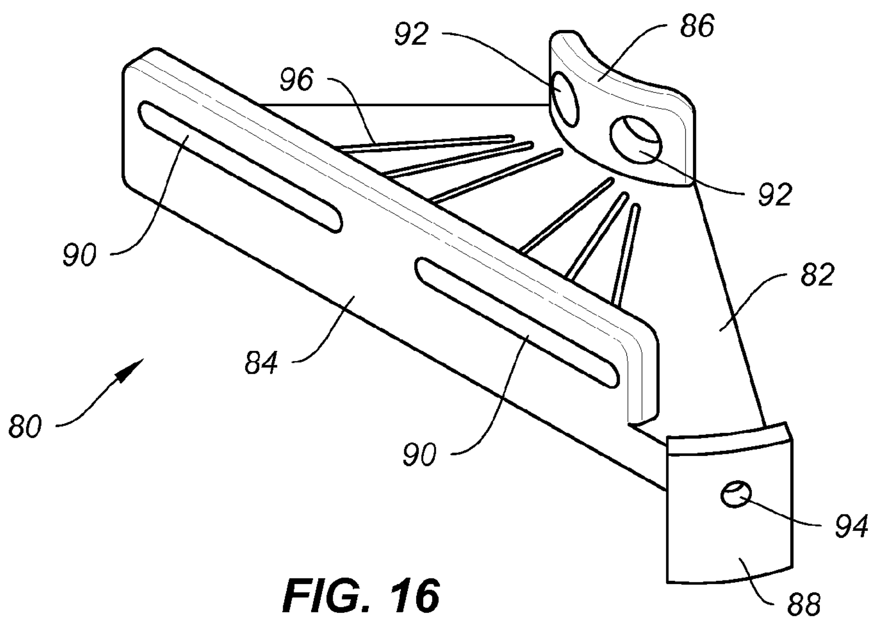
FIG. 16 is a perspective view of another exemplary embodiment of a guide instrument of the present disclosure.
Figure 17:
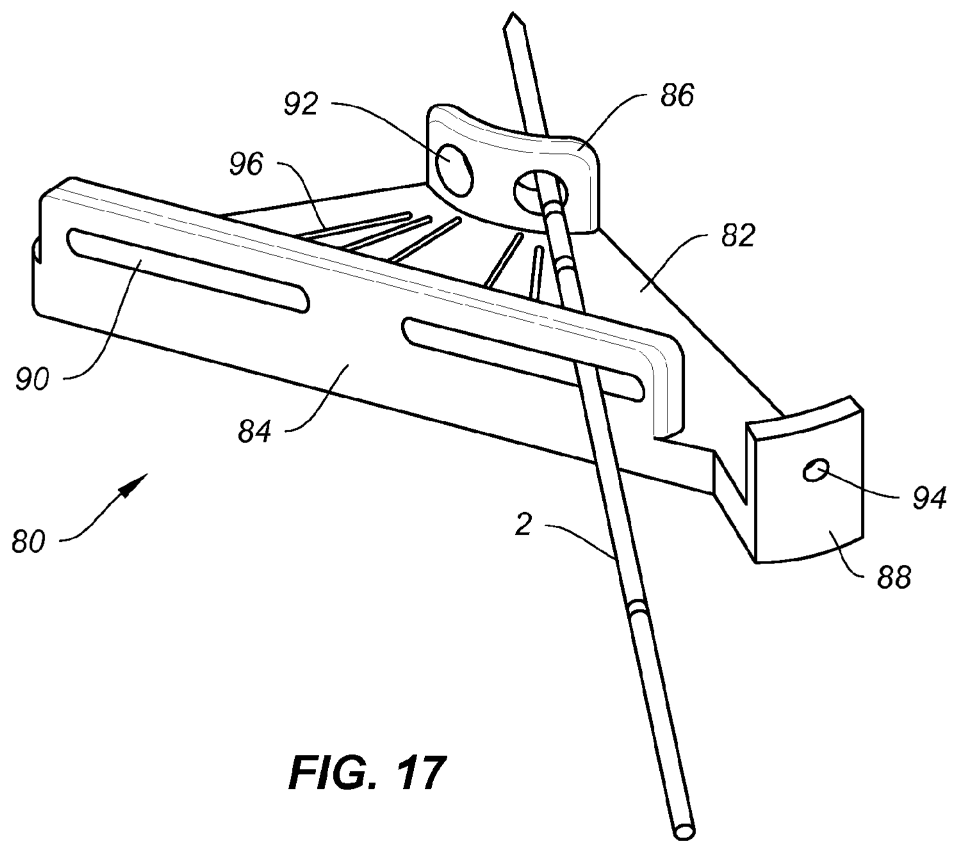
FIG. 17 shows the guide instrument of FIG. 16 with a fixation pin.

FIGS. 13-15 illustrate different MRI templates showing various trajectory paths and focal points for insertion of instruments or devices using another exemplary embodiment of a guide instrument 80 of the present disclosure, in which FIG. 13 represents an axial perspective, FIG. 14 represents an oblique perspective, and FIG. 15 represents a lateral perspective. As shown in FIG. 16, the guide instrument 80 may include a main body 82, a first lip or flange 84 on which are one or more openings 90 for receiving an instrument such as a pin 2. The openings 90 may be point of reference guide holes, for example. The main body 82 may also include a second lip or flange 86 that also includes one or more openings 92 for receiving an instrument such as a pin 2, as shown in FIG. 17. The openings 92 may be elongate, forming slots 92 that allow for infinite adjustability during insertion of the instrument or pin 2.

In addition, the main body 82 may be shaped generally like a wedge, as shown, and include visual markers 96 that act as trajectory marker guides. At one corner of the main body 82 there may be a projection from which there is a third lip or flange 88. This third flange 88 may also include an opening 94 for receiving an instrument such as a pin 2. This opening 94 may represent a distal guide instrument hole for receiving a pin 2 distally. Alternatively, this hole could serve as a trajectory guide opening for placement of a pin 2 into the anterior neck region of the talus 12 subchondral to the articulation surface with the navicular bone of the foot.

The guide instrument 80 may be considered a pre-set angular guide instrument with integrated depth control. The guide instrument 80 may allow for discrete targeting and angular trajectories which intersect at the same final depth, controlled pin placement, guidance and depth into the talus 12 of the ankle joint 10, and the ability to choose an infinite angle of insertion (via the insertion opening 92) which then converge through a common point on the guide instrument 80 for instrument or pin guidance into the bone of the ankle joint 10. The visual markers 96 may be discrete markers on the instrument 80 that correlate to available angular trajectories known. The guide instrument 80 may be hand held and manually placed to the correct anatomical location or stabilized by fixing to a foot positioner or stabilizer through, for example, a swivel or rigid connection (e.g., thread, clamp, etc.) Alternatively, the instrument 80 could be positioned to a fluoroscopic alignment bar that would locate the reference target point.

In one embodiment, the guide instrument 80 may be made of a radiolucent material. The visual markers 96 may be radiopaque and embedded within the guide instrument 80 to help orient the guide instrument 80 to reference anatomical locations.

In one exemplary method of use, MRI templates similar to those of FIGS. 13-15 may be used to locate a subchondral defect in a talus. For instance, a bone marrow lesion (BML) or bone marrow edema (BME) may be located using an axial magnetic resonance image. From this, a tangency point of the talar dome slope may be located using lateral fluoroscopy. Next, the guide instrument 80 may be positioned relative to the ankle joint 10, wherein the instrument 80 may be placed at the target area to be treated. The guide instrument 80 may be secured to the patient through, for example, attachment with a swivel arm attachment (not shown) or fixed with a pin 2 to the distal tibia or calcanaeus bone.

Figure 18:
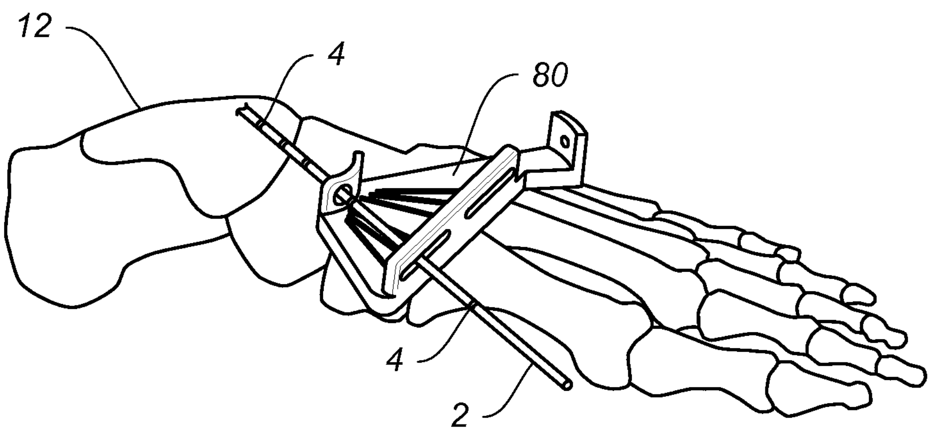
FIG. 18 shows the guide instrument and fixation pin of FIG. 17 in use on a talus of an ankle joint.
Figure 19:
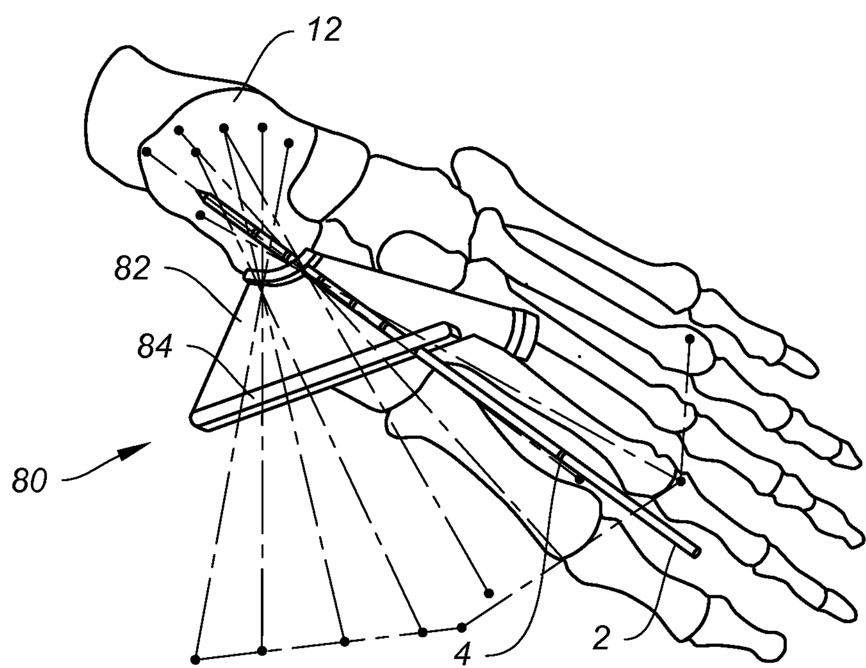
FIG. 19 shows the guide instrument of FIG. 16 with optional trajectory paths for insertion of an instrument into the talus.

Once the guide instrument 80 has been secured, a pin 2 may be inserted into the elongate slot or opening 90 on the first flange 84 and through opening 92 of the second flange 86, until a desired depth is reached (as determined by markings 4 on the pin 2, for example, that indicate that the predetermined depth has been reached.) This step is illustrated in FIG. 18. After the pin 2 has been properly inserted, a cannula (not shown) may be placed over the pin 2, and the pin 2 removed to leave only the cannula within the opening 90. An injectable material, such as a bone hardening material, may then be injected through the cannula and into the talus 12 toward the subchondral defect to be treated. The entire process may be repeated, using a different trajectory path, such as one of those shown in shadow in FIG. 19.

Suitable injectable materials can include bone fillers, but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber, polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

Figure 20:
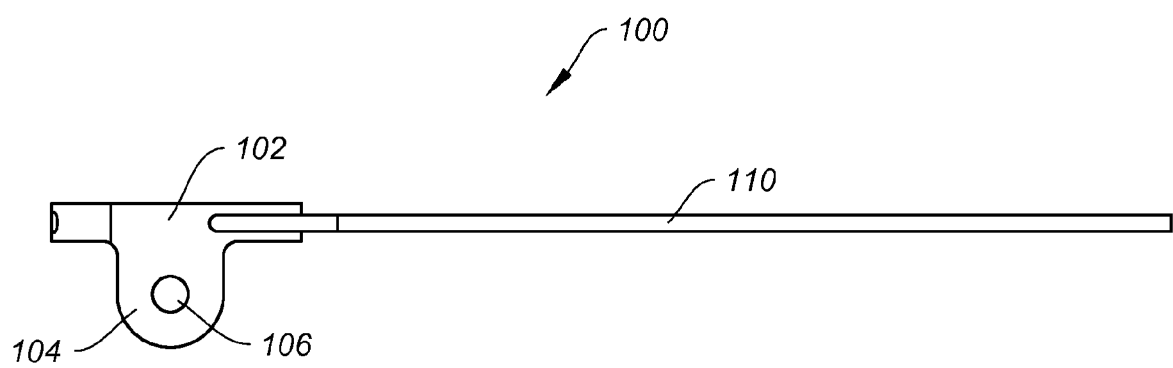
FIG. 20 illustrates a side view of yet another exemplary embodiment of a guide instrument of the present disclosure.
Figure 21:
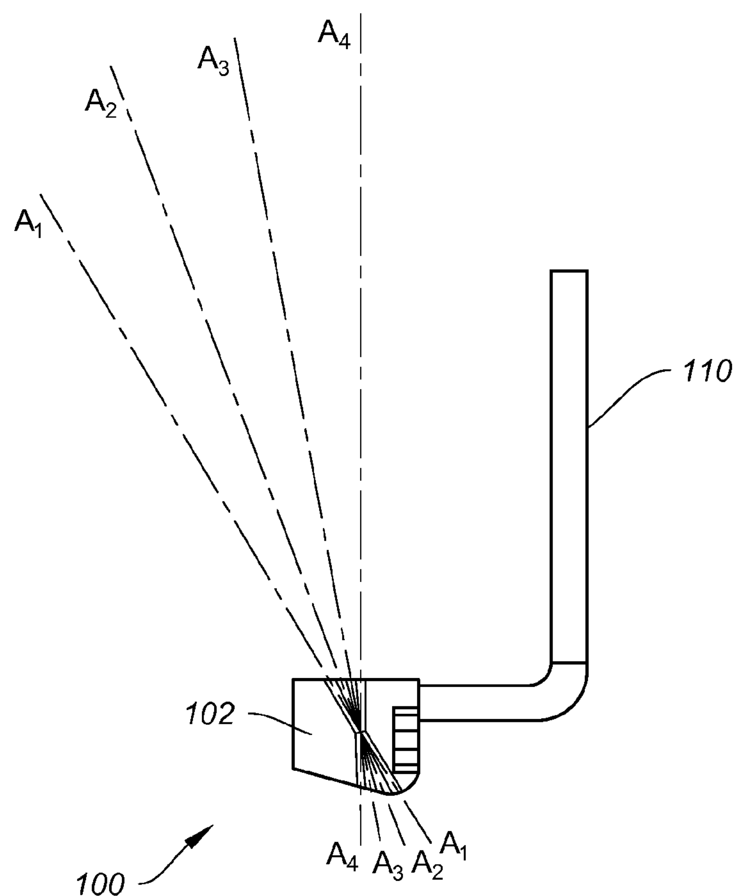
FIG. 21 illustrates a top-down view of the guide instrument of FIG. 20.
Figure 22:
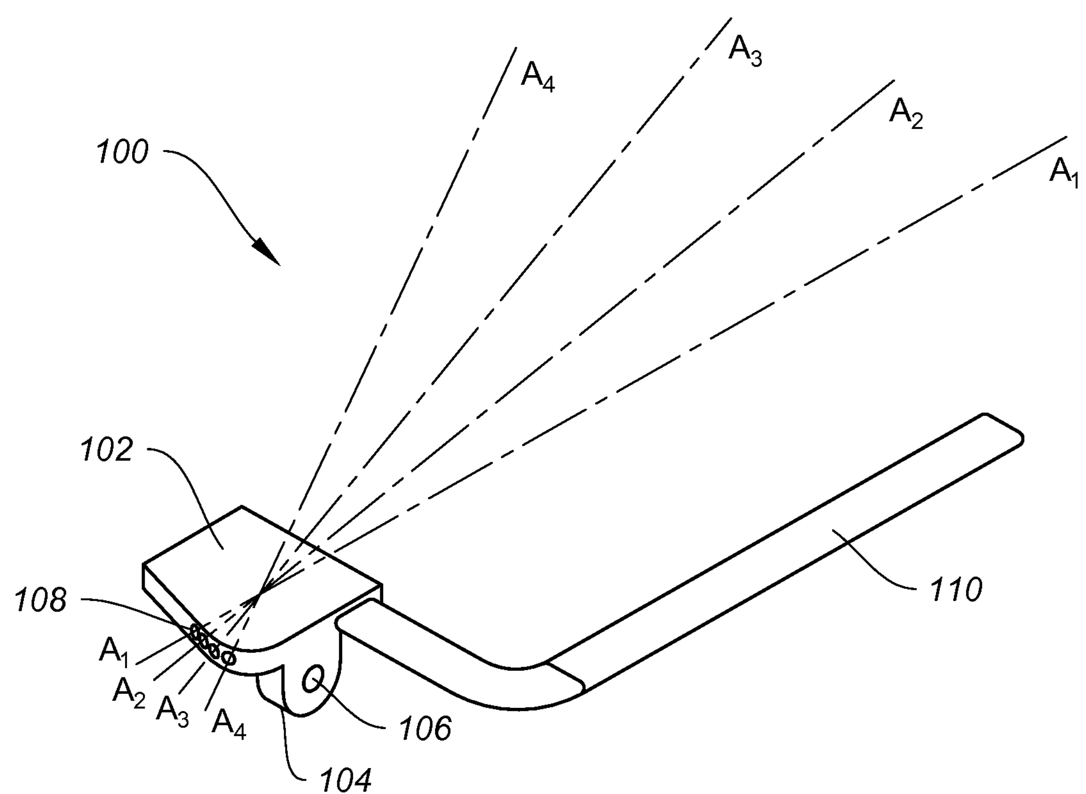
FIG. 22 illustrates a perspective view of the guide instrument of FIG. 20 with optional trajectory paths for insertion of an instrument.

FIGS. 20-22 illustrate yet another exemplary embodiment of a guide instrument 100 of the present disclosure. As shown in FIG. 20, guide instrument 100 may be used as a targeting device for locating, targeting and accessing the subchondral space of the talus, calcanaeus, or distal tibia. In one embodiment, the guide instrument 100 may be formed as a pre-set angle guide. As shown in FIGS. 21 and 22, the guide instrument 100 may comprise a main body 102 having a plurality of guide portals 108 for guiding an instrument or pin 2 toward the target area of the ankle joint 10 to be treated. The guide portals 108 may be pre-set and configured as angled trajectory portals. These portals 108 may further be spaced equally apart at a range of about 10-45 degrees, and represent an array of angular trajectories ($A_1$-$A_1$, $A_2$-$A_2$, $A_3$-$A_3$, and $A_4$-$A_4$). As with the previously described embodiments, in order to avoid damage to surrounding tissues, surgical treatment is limited to access paths through a small number of focal areas represented by the portals 108.

The main body 102 may also include a tab 104 with a through-hole 106 that allows the guide instrument 100 to connect to another equipment, such as for example, a foot positioner or stabilizer similar to the one shown in FIGS. 28-31. The tab 104 thus allows for a swivel hinge connection to be made with that foot positioner or stabilizer. In addition, the guide instrument 100 may include an alignment arm 110 that extends from the main body 102 and orients the instrument 100 to the correct pitch, roll and yaw angles. In one embodiment, the alignment arm 110 may have a flat planar configuration to indicate on fluoroscopy that the guide instrument 100 is correctly positioned (i.e., not rotated) by indication of a thin line versus a thick rectangular band.

The guide instrument 100 allows the user to control the angle of rotation in three dimensions with the pre-set angled trajectory or guide portals 108 on the main body 102. The alignment arm 110 indicates height and sagittal angulation of the portals 108, while the ability to swivel the instrument 100 via the swivel hinge attachment to the foot stabilizer allows for both transverse and sagittal angulation to the desired target point on the ankle joint 10. A pin can be placed into one of the guide portals 108 to help verify transverse and sagittal angulation or orientation relative to the talus or calcaneous bone under fluoroscopic imaging.

Figure 23:
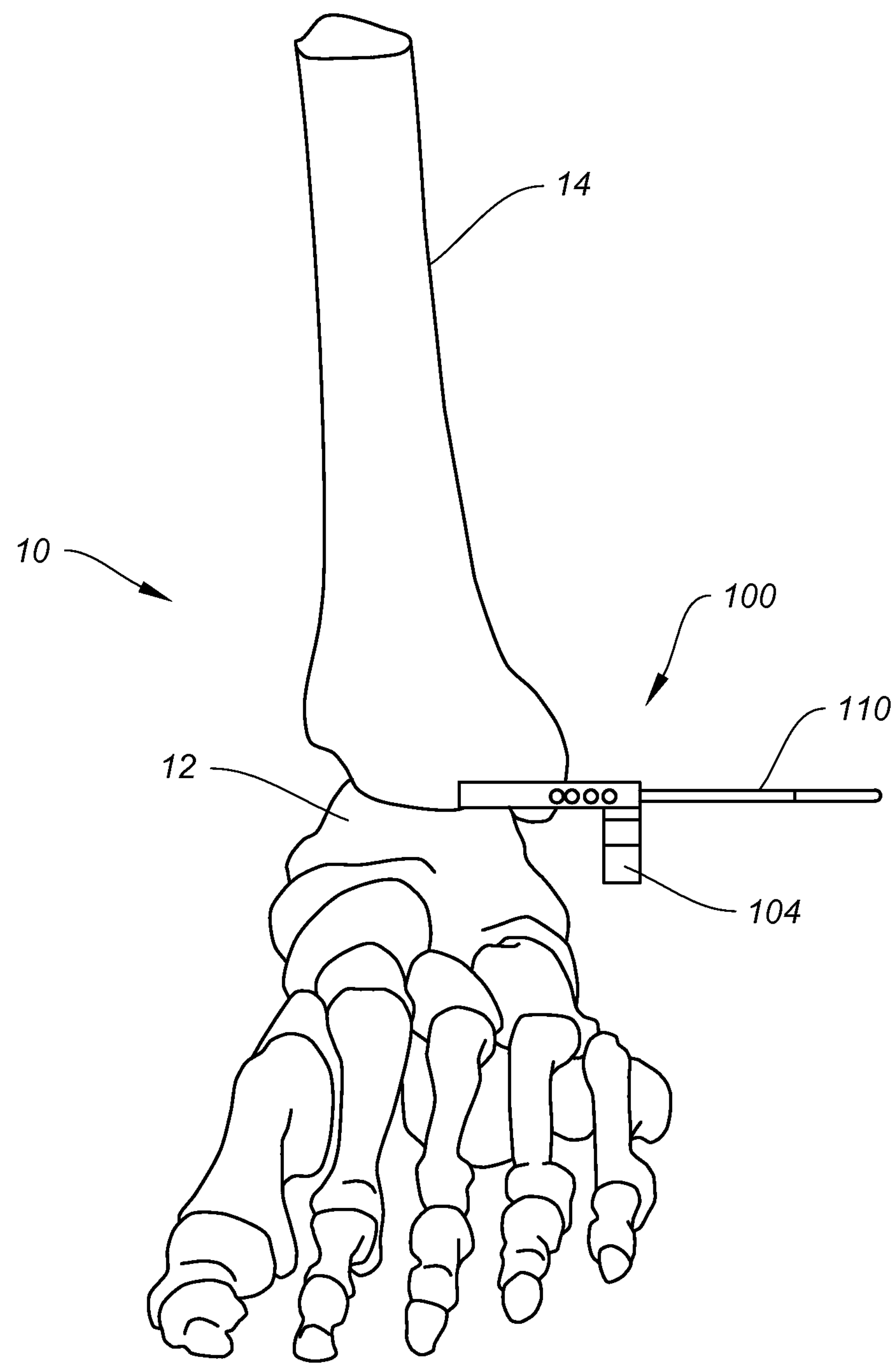
FIG. 23 shows the guide instrument of FIG. 20 in use with an ankle joint.
Figure 24:
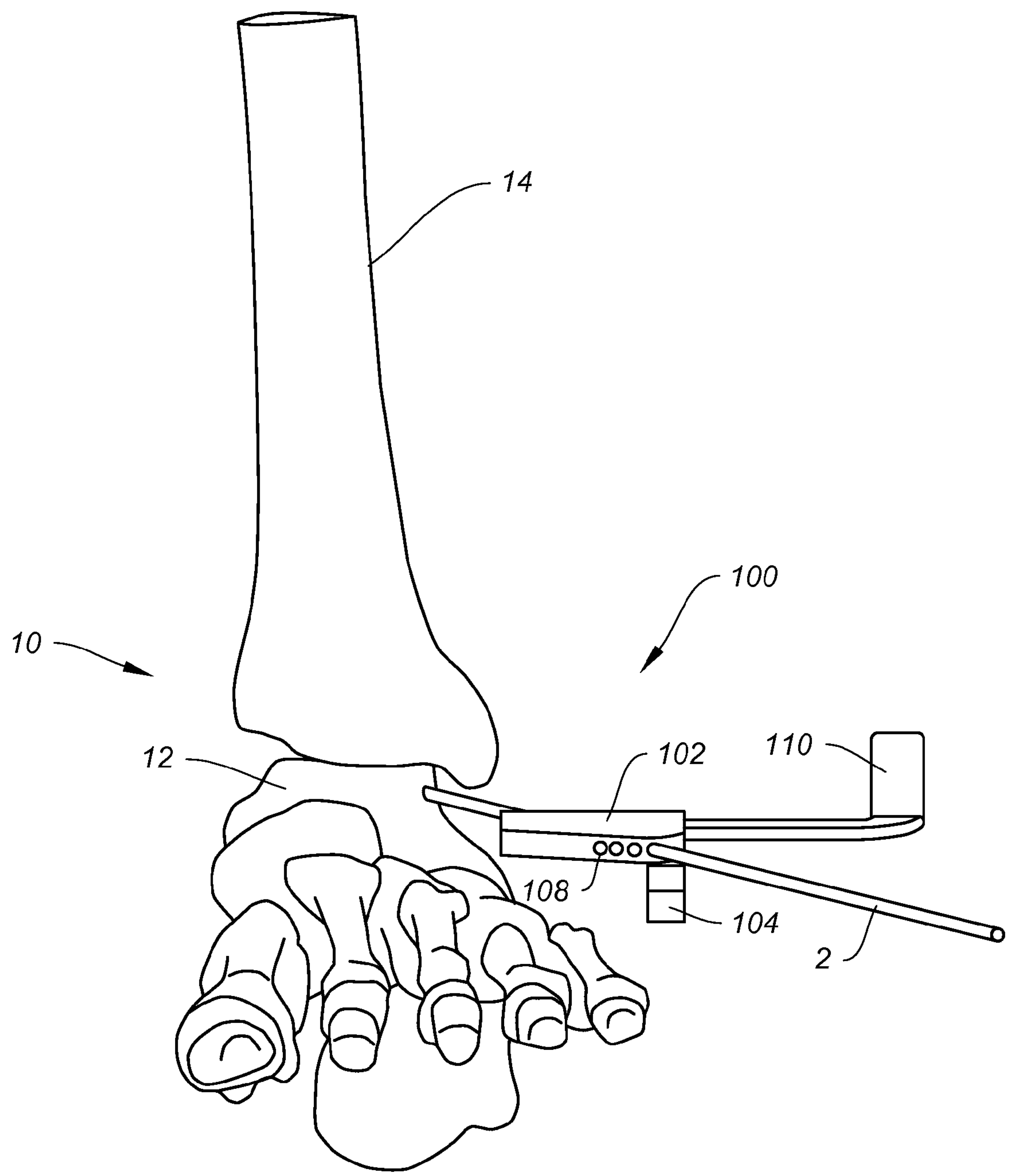
FIGS. 24-27 illustrate an exemplary method of using the guide instrument of FIG. 20 to treat an ankle joint.
Figure 25:
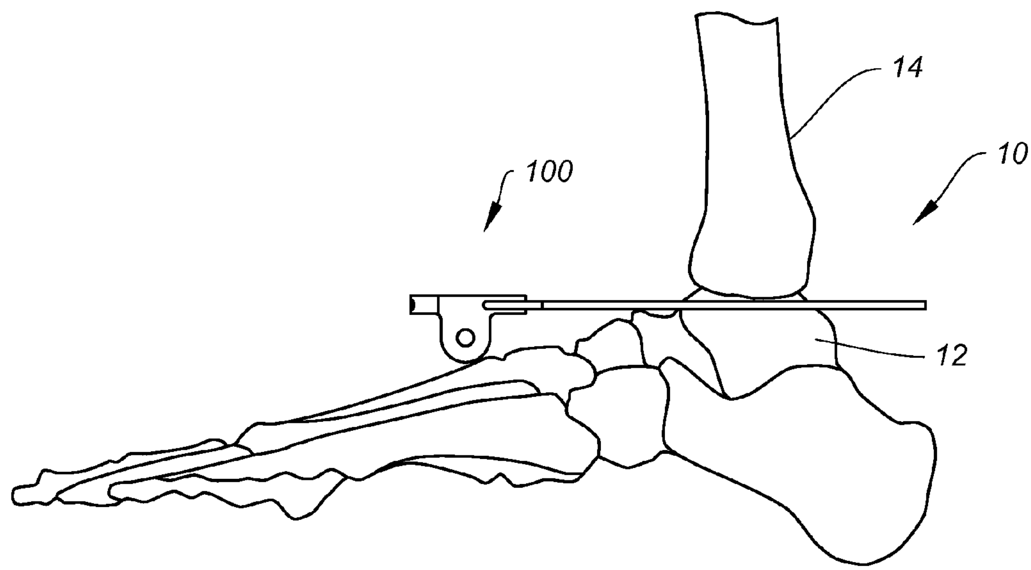
Figure 26:
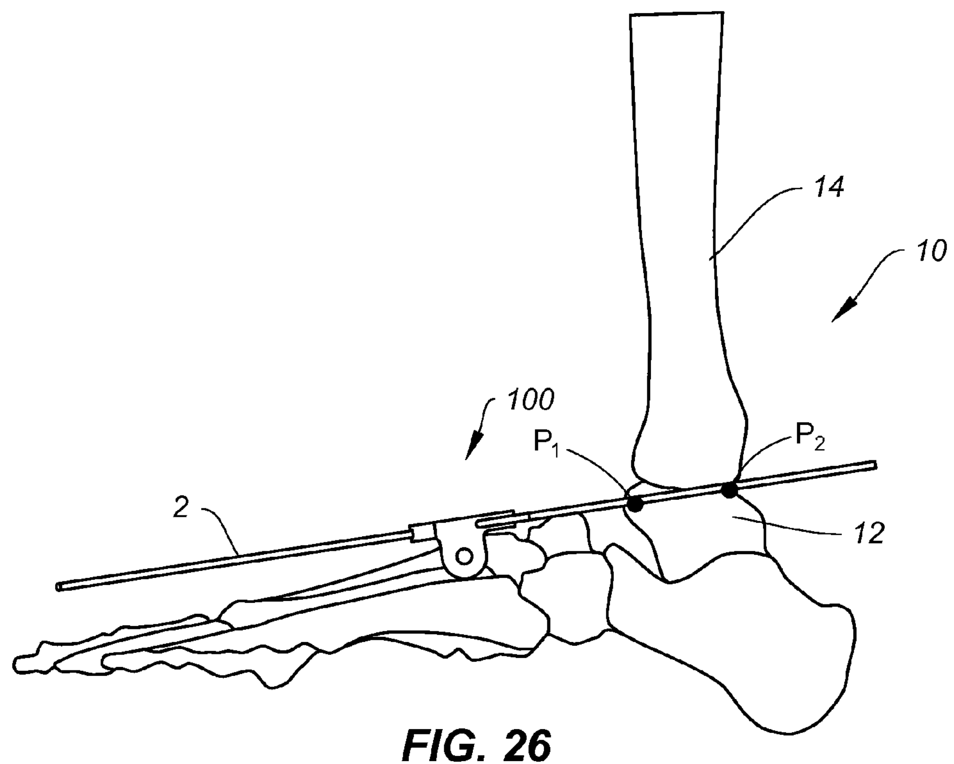
Figure 27:
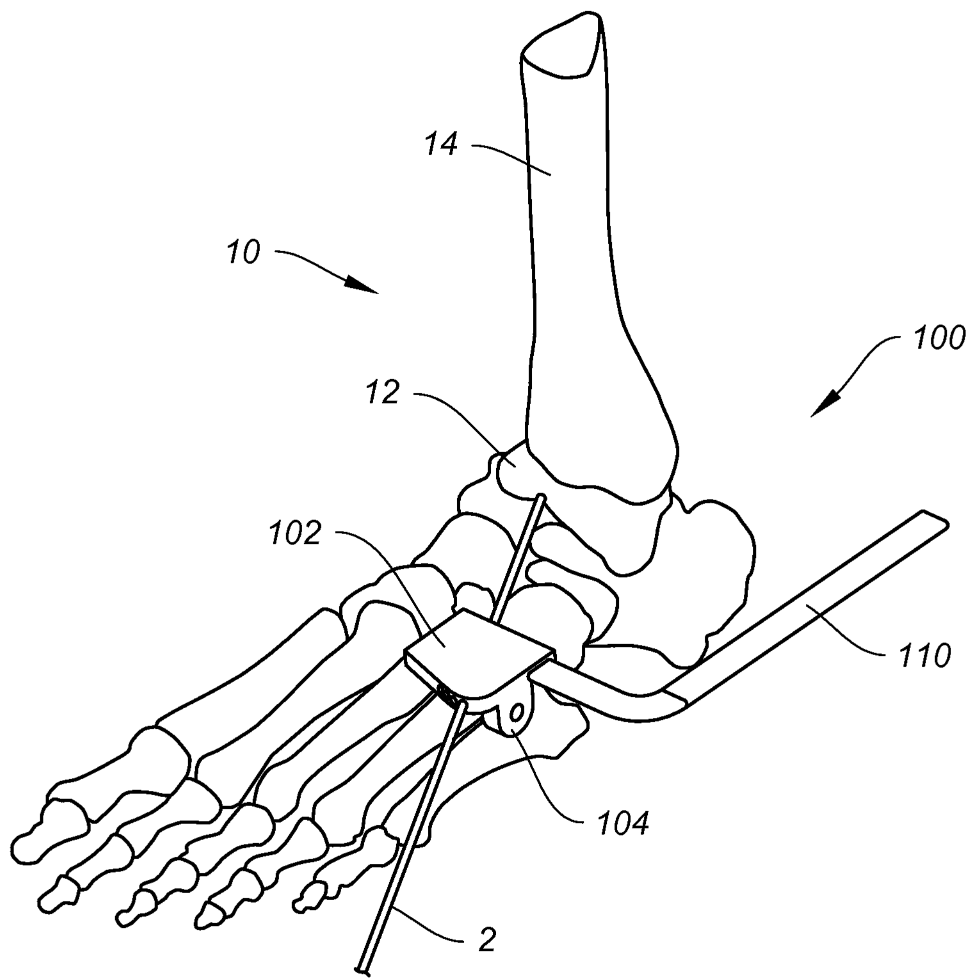

FIGS. 23-27 show one exemplary method of using the guide instrument 100. First, the guide instrument 100 may be aligned to the dome of the talus 12, as shown in FIG. 23. The guide instrument 100 allows an instrument, such as a fixation element like a pin 2, may be inserted through one of the portals 108 of the guide instrument 100, as shown in FIG. 24. The guide instrument 100 may then be aligned height-wise, such as to the height of the talar dome subchondral defect (e.g., lesion or edema), as shown in FIG. 25. Then, the guide instrument 100 may be aligned to reference points $P_1$ and $P_2$ on the talar dome, where $P_1$ and $P_2$ represent points along a line of tangency, for example (FIG. 26). After alignment, the guide instrument 100 provides guided access of an instrument or pin 2 through one of the pre-set angled portals 108 and to the target location of the ankle joint 10 to be treated, as shown in FIG. 27. Limiting the surgeon's access paths to the bone to the few select focal areas represented by the pre-set angled portals 108 avoids undesired or accidental damage to surrounding tissues.

Figure 28:
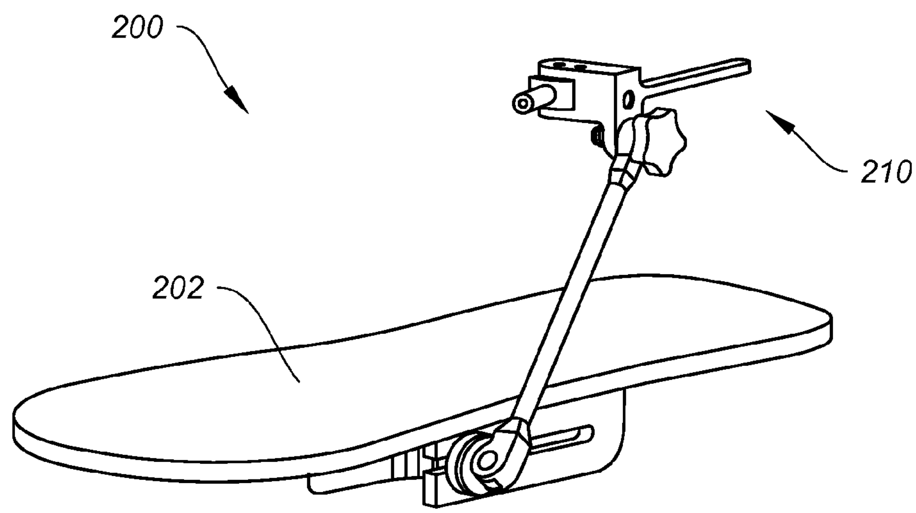
FIG. 28 illustrates a perspective view of an exemplary embodiment of a foot stabilizer and guided access instrument of the present disclosure.
Figure 29:
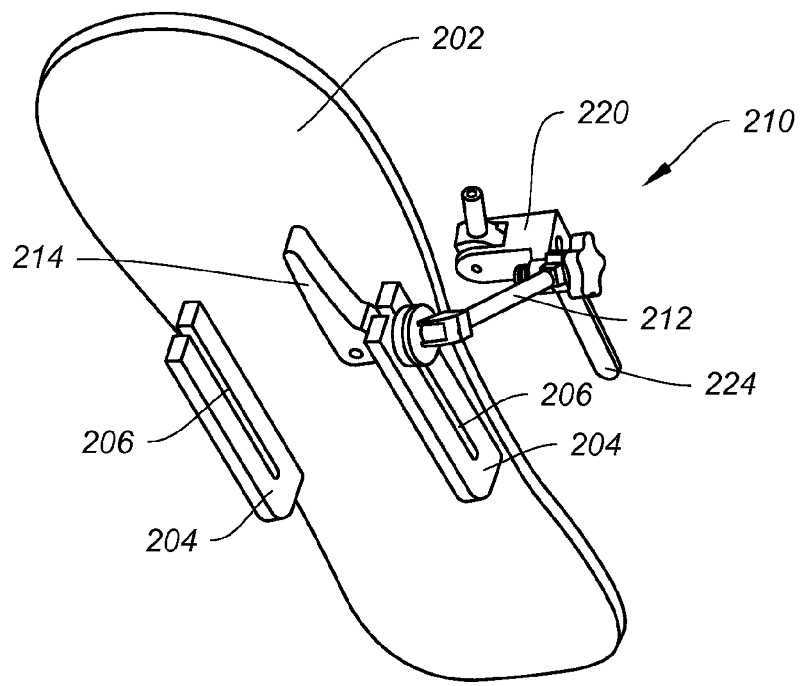
FIG. 29 illustrates another perspective view of the foot stabilizer of FIG. 28.

FIGS. 28 and 29 illustrate an exemplary embodiment of a foot stabilizer and guided access instrument 200 of the present disclosure. The foot stabilizer and guided access instrument 200 includes a platform 202 that may be secured to the foot to be treated using ties, bands, straps, Velcro, belts, suspenders, etc. as may be commonly employed in the art. The guidance instruments previously described and shown, as well as other navigation or guidance instruments for guided access into a joint, may be coupled to the foot stabilizer and guided access instrument 200. In one embodiment, the foot stabilizer and guided access instrument 200 may be provided with its own guided access component 210, as shown in FIG. 29. This guided access component 210 may be adjustable (i.e., mobile) until it is locked or fixed into position.

It is contemplated that this foot stabilizer and guided access instrument 200 be adjustable in length as well as width, and be rigidly secured to a foot with the securing elements just described. Of course, it is also contemplated that the foot stabilizer and guided access instrument 200 could be provided with a built-in foot attachment system, such as for example, a crank similar to those in ski boots, or a net-like band of Velcro such as found in sandals, so long as the attachment system does not impede in the access to be desired. While the foot stabilizer and guided access instrument 200 may be entirely rigid, it is also possible for the instrument 200 to be rigid in part. And although the platform 202 of the foot stabilizer and guided access instrument 200 is shown here as having a relatively flat surface, it is of course contemplated that the platform 202 could also have a contoured surface to match the foot more anatomically and provide a better fit. It is also contemplated that the foot stabilizer could have an extension that secures to the back of the calf of the leg using securing elements as previously mentioned above. With this extension, the device could secure the angular position of the foot relative to the lower leg or tibia in order to provide more accurate controlled access to the ankle.

Turning now to FIG. 29 and to the details of the foot stabilizer and guided access instrument 200, the foot stabilizer and guided access instrument 200 may include a pair of tracks 204 extending from the platform 202, each track 204 having a slotted rail 206 for translational movement of an attachment arm 212. The tracks 204 allow the user to place this arm 212 on either the left or right side of the foot stabilizer 200. The arm 212 may be attached to the track 204 with a cam 214, as shown. Attached to the arm is an adjustable guided access component 210 that may be fixed into position to allow guided access of an instrument or pin 2 into the bone of the foot to be treated. In other embodiments, the guided access component 210 and arm 212 may be fixed to the platform 202 with screws or other known fixation elements, so long as the arm 212 remains securely attached to the platform 202 of the foot stabilizer 200.

Figure 30:
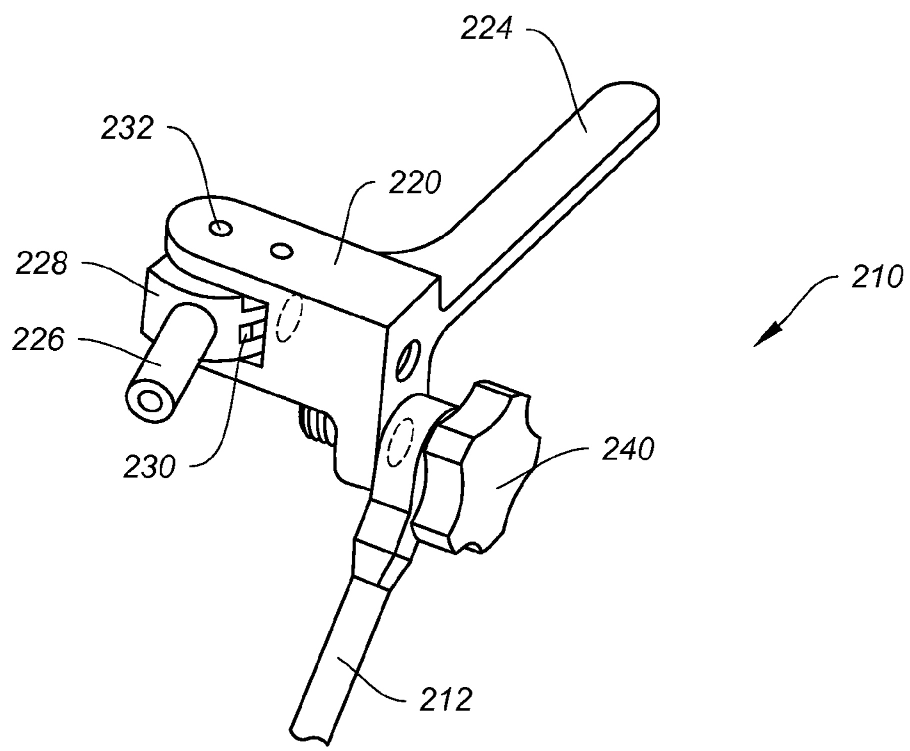
FIG. 30 illustrates an enlarged view of the guide component of the foot stabilizer and guided access instrument of FIG. 28.

As shown in greater detail in FIG. 30, the guided access component 210 may include a main body 220 from which extends a visualization bar 224. The visualization bar 224 serves as a fluoroscopic visual marker that allows the user to align the instrument to anatomical markers under fluoroscopy. The body 220 also includes a pivotable hub 228 from which extends a portal 226 that serves as a guided access path for an instrument or pin 2 to be inserted therethrough. This pivotable hub 228 is rotatable within a slot of the body 220. As illustrated, the pivotable hub 228 may include divots 230 that may work with a ball plunger inside the mail body 220 to provide an adjustable stop or control mechanism for alignment of the portal 226. The pivotable hub 228 may thus click into a desired position. For instance, the divots 230 could allow positioning of the portal 226 to direct the trajectory path of the pin 2 toward selected points on the bone to be treated. The divots 230 also may limit the path of approach, preventing dangerous approaches to the bone. Pinned slots provided on the body 220 would cooperate with the pivotable hub 228 to prevent over-rotation. The guided access component 210 may be secured to the attachment arm 212 with a threaded mechanism such as with knob 240 as shown.

Figure 31:
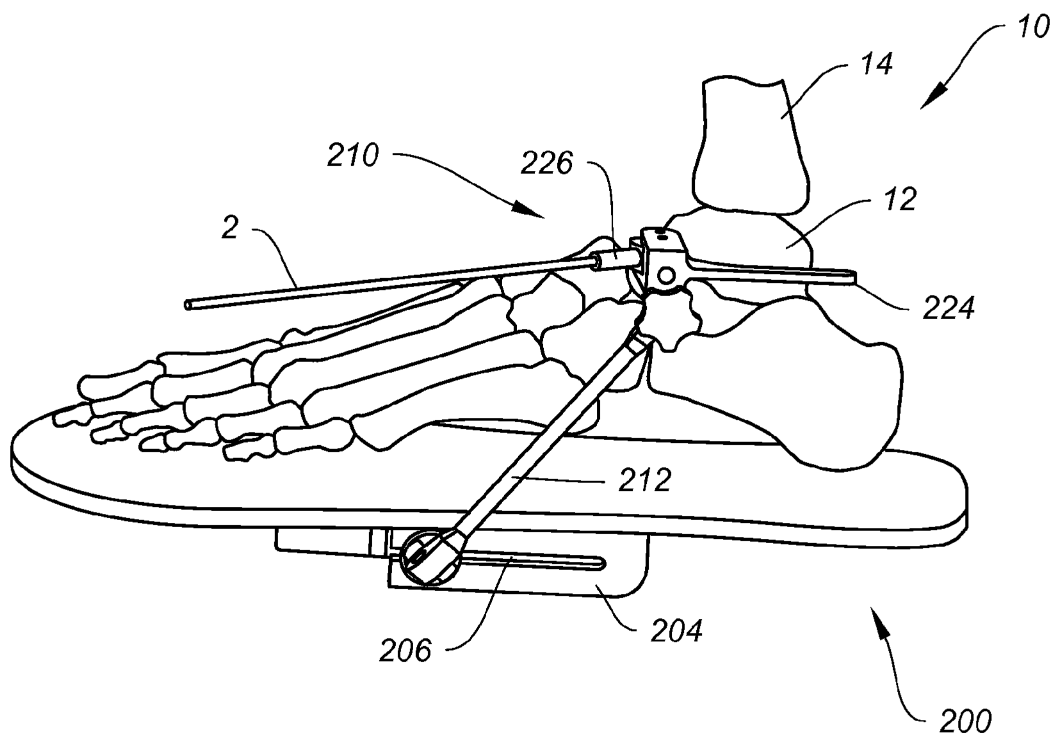
FIG. 31 shows a side view of the foot stabilizer and guided access instrument of FIG. 28 in use with a foot.

During use, the arm 212 may be shifted along the slotted rail 206 in a translational direction, but could also pivot as well. The attachment arm 212 may be secured to the track 204 with the cam 214. The portal 226 can be configured as a tube having a length and overall geometric shape that is suitable to support a pin 2, without bending and skiving of the pin 2 during use, as shown in FIG. 31. The ability to adjust the attachment arm 212 as well as the guided access component 210 relative to one another as well as to the platform 202 allows the user greater flexibility in aligning the portal 226 in any number of configurations. Thus, the foot stabilizer and guided access instrument 200 may be useful for targeting a number of locations on or near the foot, such as the talus, tibia, fibula, calcaneous, etc.

Figure 32:
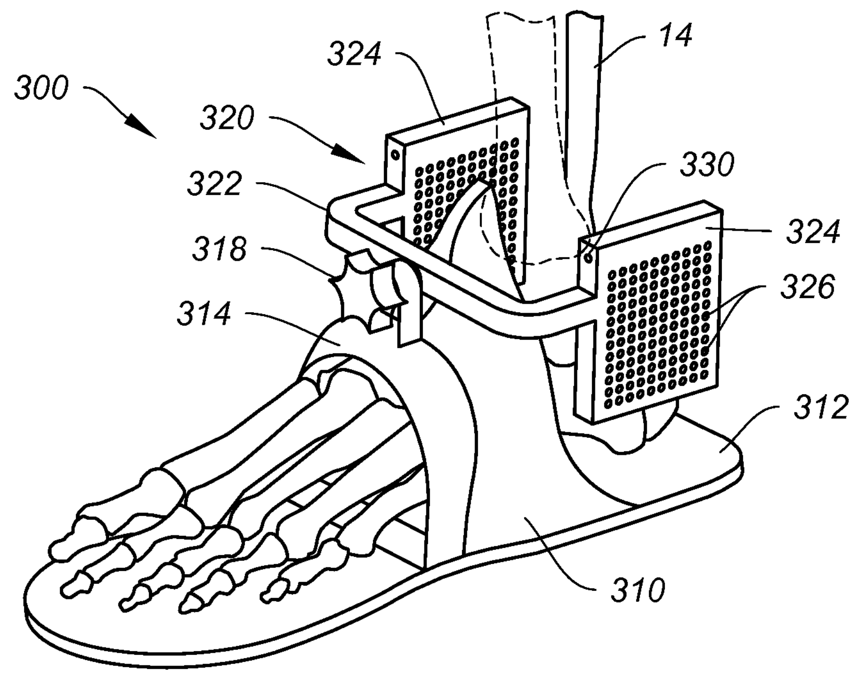
FIG. 32 is a perspective view of still another exemplary embodiment of a foot stabilizer and guided access instrument of the present disclosure.
Figure 33:
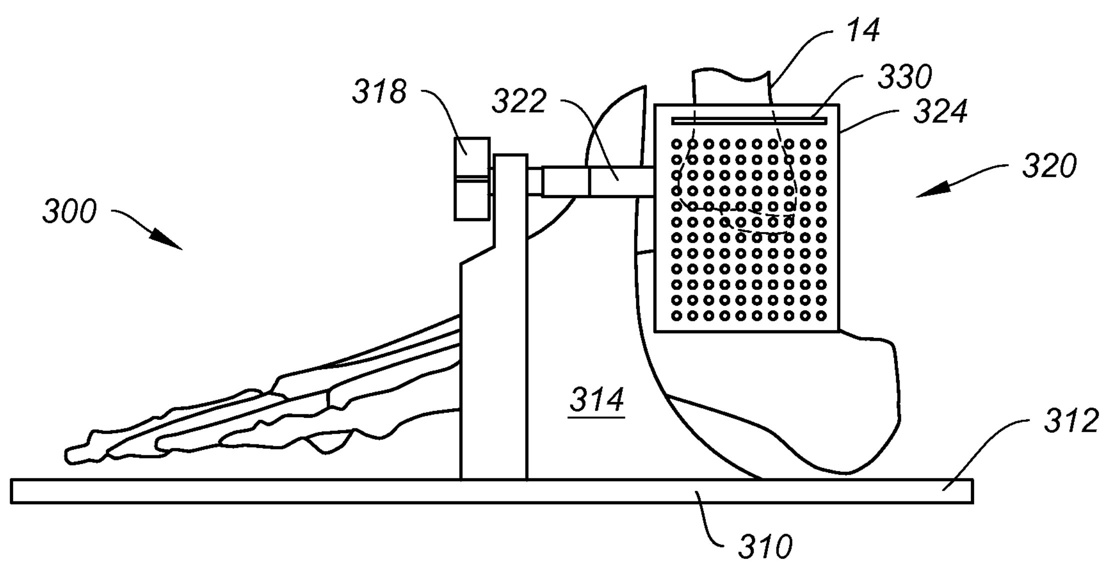
FIG. 33 is a side view of the foot stabilizer and guided access instrument of FIG. 32.

FIGS. 32 and 33 illustrate another exemplary embodiment of a foot stabilizer and guided access instrument 300 of the present invention. As shown the instrument 300 may comprise a foot stabilizing component 310 and a guided access component 320. The foot stabilizing component 310 may include a platform 312 attached to which is a foot band 314 that surrounds a portion of the patient's foot. The foot band 314 may be unitary or it may be formed in portions. The guided access component 320 comprises a bar 322 that attaches to the foot band 314 by way of a threaded connection, such as for example, knob 318 as shown. The bar 322 extends into grid panels 324 on which are a plurality of openings or portals 326 for guiding an instrument or pin 2 therethrough. The grid panels 324 may also include visualization aids, such as for example fluoroscopic markers 330.

In use, the patient's foot may be secured to the foot stabilizing component by means of the foot band 314, which could be ties, straps, bands, belts, etc. as previously described. The grid panels 324 are rotated so as to be aligned when the foot is in a true lateral position. The alignment may be achieved using the fluoroscopic markers 330 provided on the grid panels 324. For instance, the markers 330 may be configured to overlap when the foot is in the true lateral position. The guided access component 320 may be rotated relative to the foot stabilizing component 310 and then fixed into place with the knob 318. The openings or portals 326 would allow access to multiple bones, for additional flexibility during surgery.

Figure 34:
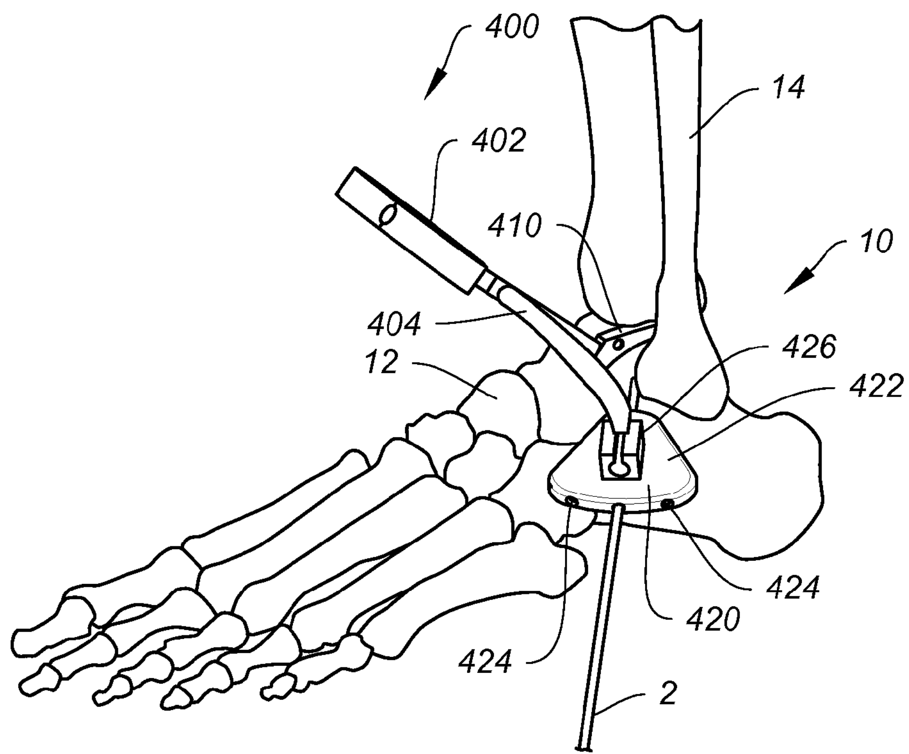
FIG. 34 is a perspective view of an exemplary embodiment of an ankle probe of the present disclosure in use on a foot.
Figure 35:
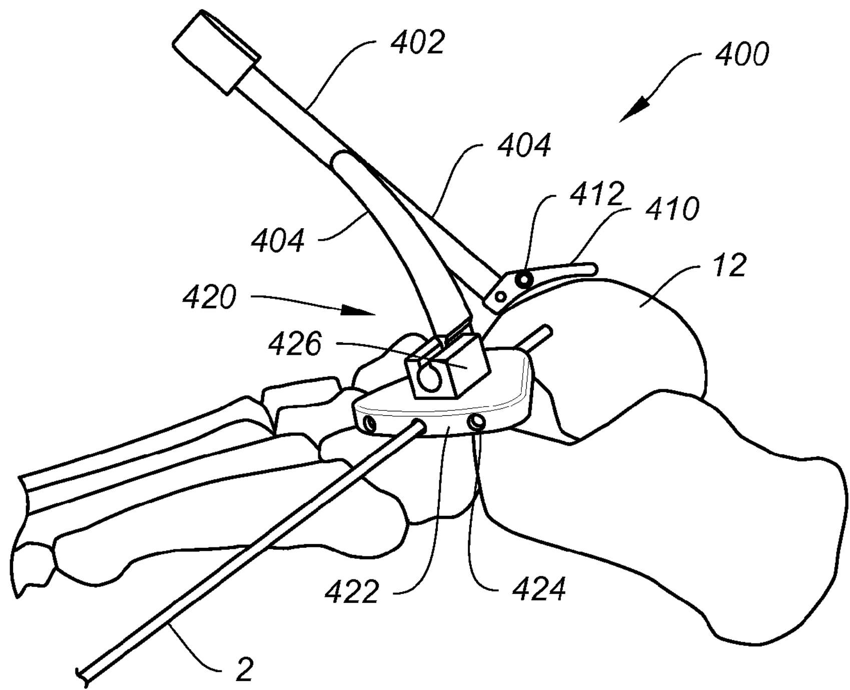
FIGS. 35 and 36 are enlarged perspective views of the ankle probe of FIG. 34 in use with a foot.
Figure 36:
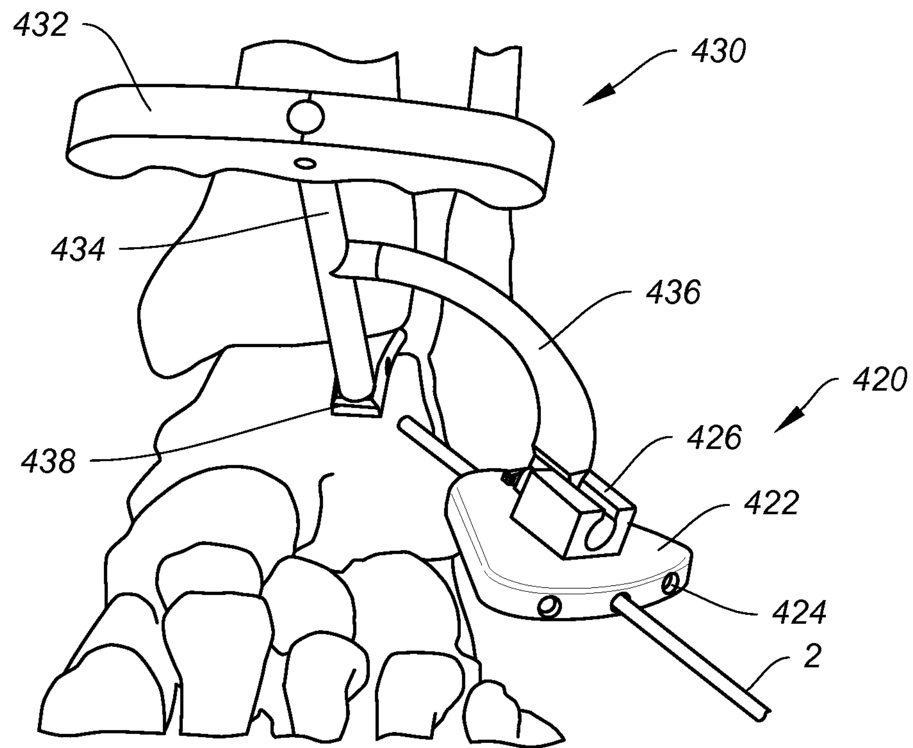

FIGS. 34-36 illustrate an exemplary ankle probe 400 of the present disclosure. The ankle probe 400 is intended to rest between the talus 12 and the distal tibia 14, as shown. The ankle probe 400 is configured to allow more direct contact with bone on either the left or right side of the ankle joint 10 to control horizontal positioning. At least some or all of the ankle probe 400 may be made with radiopaque material to be visualized under fluoroscopy. Additionally, the ankle probe 400 may include a hole or other visual indicator to allow the user to verify that it is in a true lateral position relative to bone.

As shown, the ankle probe 400 comprises a handle 402 that extends into a pair of legs 404. One of the legs 404 terminates into a foot rest or bone rest 410. As shown in FIG. 35, the rest 410 may be contoured and configured to rest against the talus 12. The rest 410 may be angularly adjustable relative to the leg 404 for ease of use. In one embodiment, the rest 410 may include an alignment hole 412 that would show up when the probe 400 is in true lateral position. The alignment hole 412 may also be placed so as to correspond to the bone (e.g., bottom of talar dome), allowing for alignment with an anatomical landmark.

The other leg 404 may be attached to a guide body 420 by way of a slotted receiver 426. This allows for easy removal of the guide body 420 from the handle 402 without affecting a pin 2 that has been inserted therethrough. The guide body 420 may include a platform 422 on which is provided a plurality of portals 424 for guided access of a pin 2 or other instrument to a region of the ankle joint 10. The portals 424 may be angularly pre-set so that the portals 424 target specific locations in the bone. Again, in order to avoid damage to surrounding tissues, surgical treatment is limited to access paths through a small number of focal areas represented by the portals 424. The handle 402 allows for control of the probe 400 and keeps the user's hand away from any C-arm shots that may be needed during surgery.

FIG. 36 illustrates another embodiment of the ankle probe 400 in which the handle 432 and the first leg 434 is straight, taking the shape of a T-bar, while the other leg is curved into a sweeping arm 436. The straight leg 434 may terminate into a foot 438 that is configured to rest on bone. The sweeping arm 436 may be configured to cooperate with the guide body 420 by sliding engagement with the slotted receiver 426 of the guide body 420. As shown, the ankle probe 400 may be positioned between the talus 12 and the tibia 14, resting against the fibula. It is contemplated, however, that the probe 400 could also be positioned adjacent to the malleolus with a differently shaped sweeping arm for lateral approaches. Various configurations are contemplated in which the handle or guide may be different to address any of the bones of the ankle joint 10.

Figure 37:
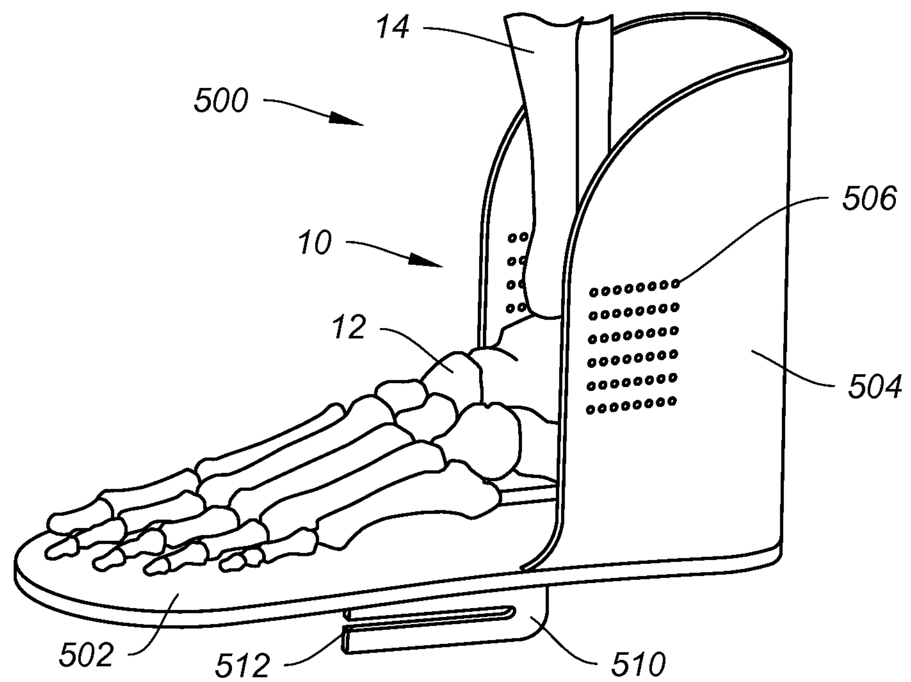
FIG. 37 is a perspective view of even still another exemplary embodiment of a foot stabilizer and guided access instrument of the present disclosure.

FIG. 37 illustrates an exemplary embodiment of still another foot stabilizer and guided access instrument 500 of the present disclosure. The instrument 500 may be configured to secure the foot to be treated during an MRI. Thus the instrument 500 may be made of a material that is visible on MRI. As shown, the instrument 500 shares similar features to the previously described foot stabilizer and guided access instruments, such as a platform 502 from which extends at least one track 510. The track may include a slotted rail 512 for attachment to other equipment, such as those already described above. These equipment may optionally be attached to the instrument 500 during the MRI, or they may be attached after the MRI visualization, and marked to be mapped to the MRI. Extending from the platform 502 is a boot 504 containing a plurality of portals 506 for guided access to the ankle joint 10. The multiple openings provided by the portals 506 allow for a variety of trajectories or approaches to the ankle joint 10 as well as for attachment to the tibia 14 or other bone.

In use, the exact approach of the instrument or pin 2 would be determined using MRI and viewing the relation between the subchondral defect (BME or BML, for example) and the instrument 500. With this information, the exact portal(s) 506 may be selected to achieve the desired trajectory or path of insertion.

Figure 38:
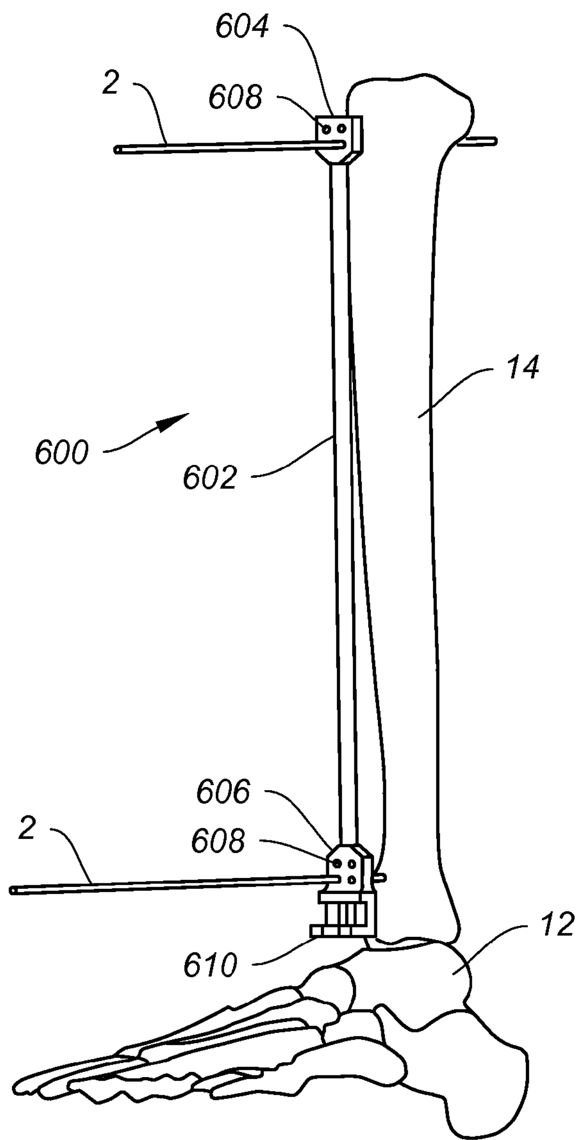
FIGS. 38 and 39 illustrate perspective views of an exemplary embodiment of a tibial attachment instrument of the present disclosure in use with a tibial bone.
Figure 39:
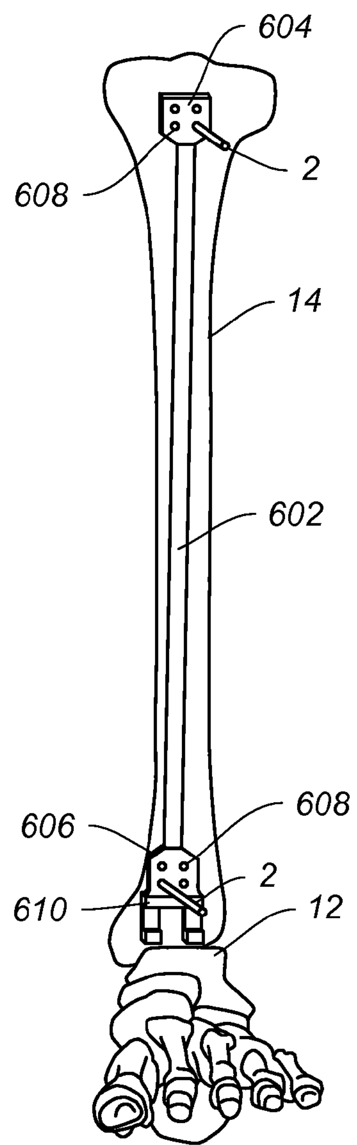
Figure 40:
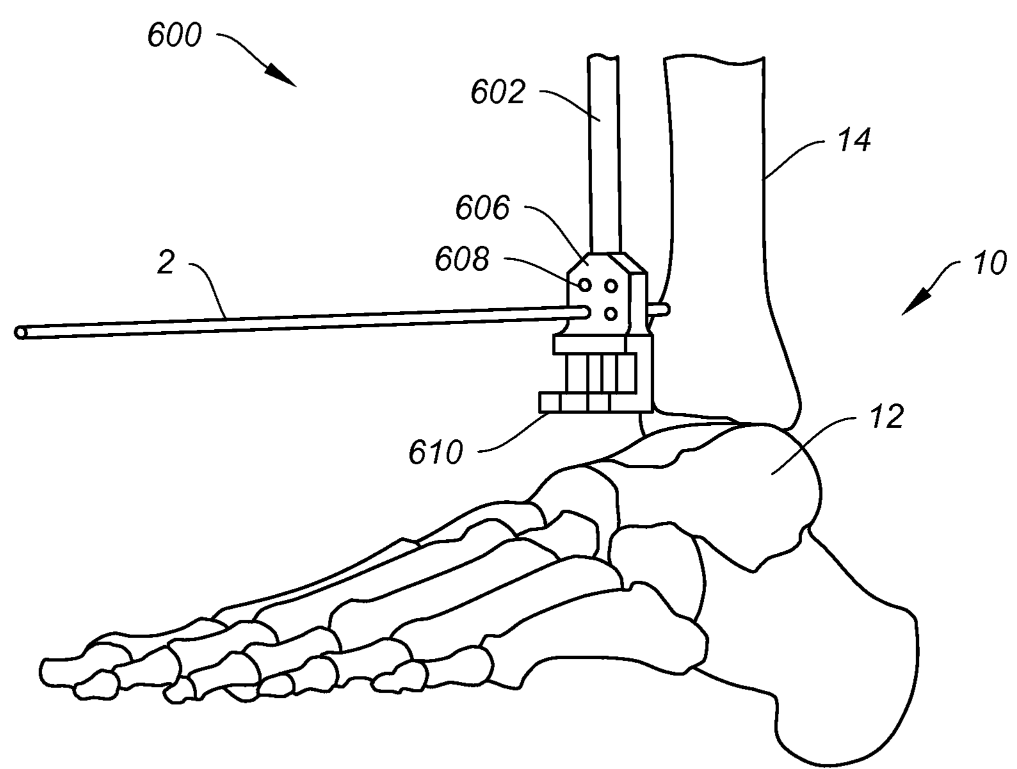
FIG. 40 is an enlarged view of the tibial attachment instrument of FIGS. 38 and 39 in use with a tibial bone.

FIGS. 38-40 illustrate an exemplary embodiment of a tibial attachment instrument 600 of the present disclosure. This tibial attachment instrument 600 provides one manner of treatment by allowing the surgeon to target a different access point at or near the small joint. The instrument 600 is intended to attach to the tibia 14 and allow other guides or instruments to then be secured to it as well. In this example, the distal tibial bone is targeted. Much like in a knee joint where either or both of the tibial and femur can be targeted for subchondral treatment, the distal tibia and/or the talus or calcaneous bone may be targeted in ankle joint treatment.

As shown, the tibial attachment instrument 600 comprises an elongate shaft 602 that terminates into a proximal end plate 604 and a distal end plate 606, both plates having at least one hole 608 for receiving an instrument such as a fixation element like a pin 2. In addition, the distal end plate 606 includes a notched tab 610 to allow other guide instruments and access instruments to attach to this tibial attachment instrument 600.

Although the instrument 600 is shown as being attached to the tibia 14 with pins 2, it is contemplated that other known fixation elements may be used, such as straps, belts, ties, etc. The instrument 600 provides a secure connection for other guides that target specific bones of the ankle joint 10 to be attached to a stable construct. The elongate shaft 602 is configured to span a substantial length of the tibia 14 while being secured to the bone at the proximal and distal ends. The notched tab 610 allows the other guides and instruments to be adjustably attached to the instrument 600, such as by a detachable interference fit. However, other fixation mechanisms may also be employed, such as a ball plunger, cam or set screw.

In another embodiment, the elongate shaft 602 may be curved to match a contour of the tibial bone 14. The shaft 602 may be made of a radiopaque material to assist in positioning with fluoroscopy. In addition, the instrument 600 may be provided with markers to match anatomical landmarks for purposes of positioning and aligning the instrument 600. The tibial attachment instrument 600 allows individualized and precise alignment to a patient's natural anatomy, in turn allowing more accurate guide attachment and bone targeting.

Figure 41:
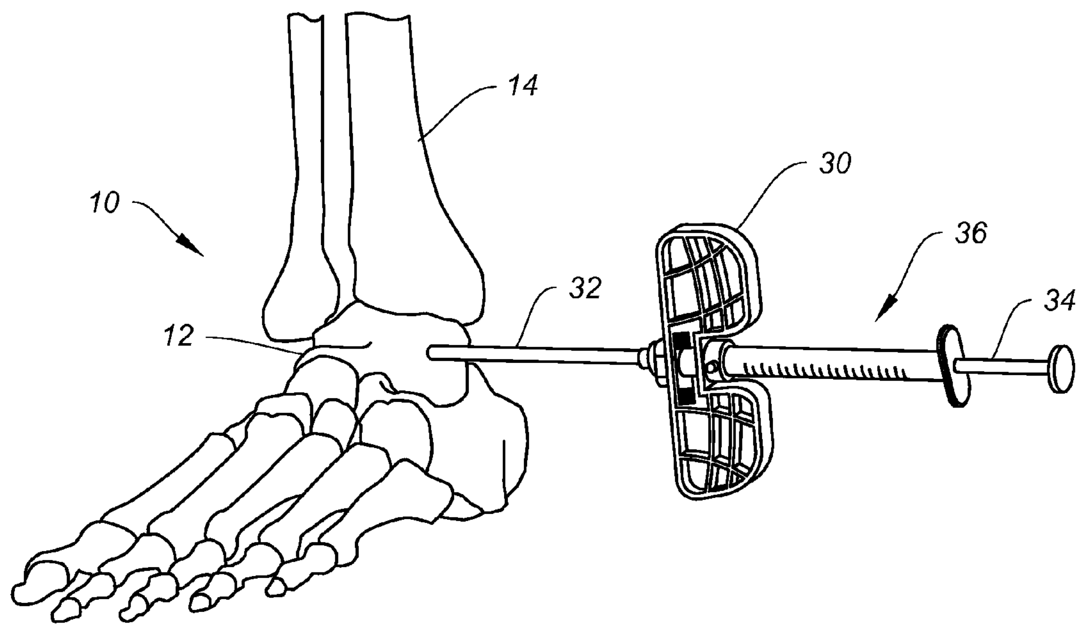
Figure 42:
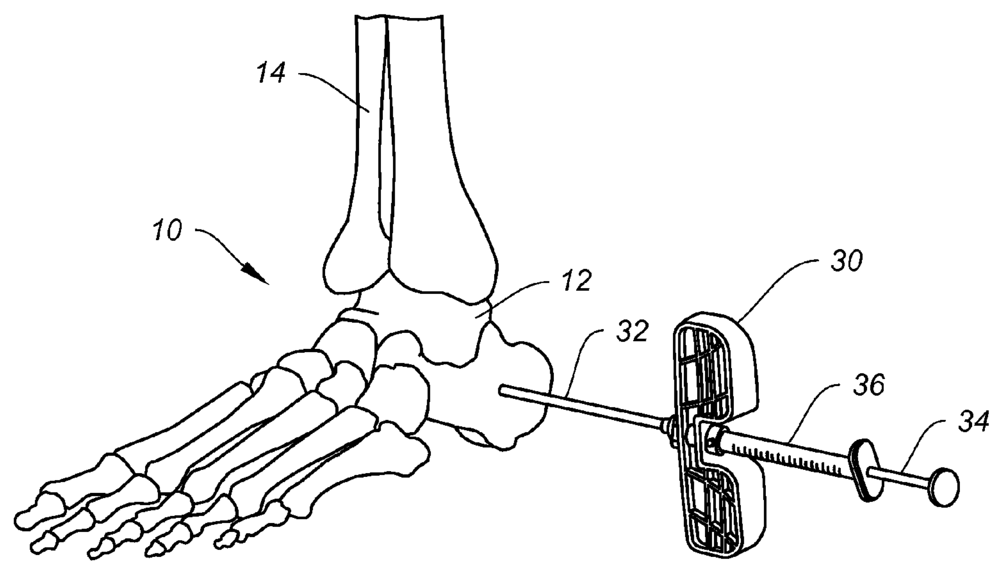
Figure 43:
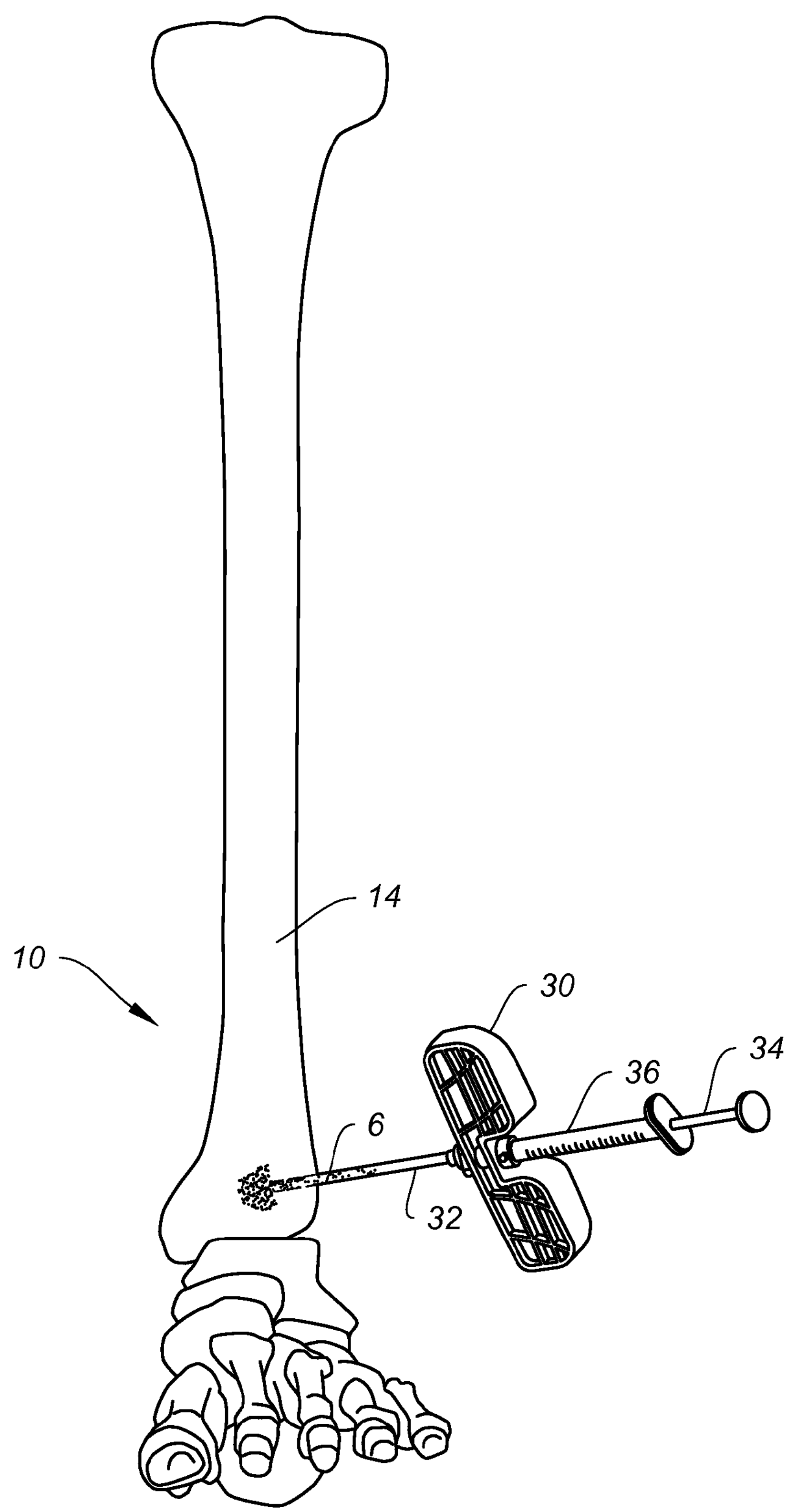
Figure 44:
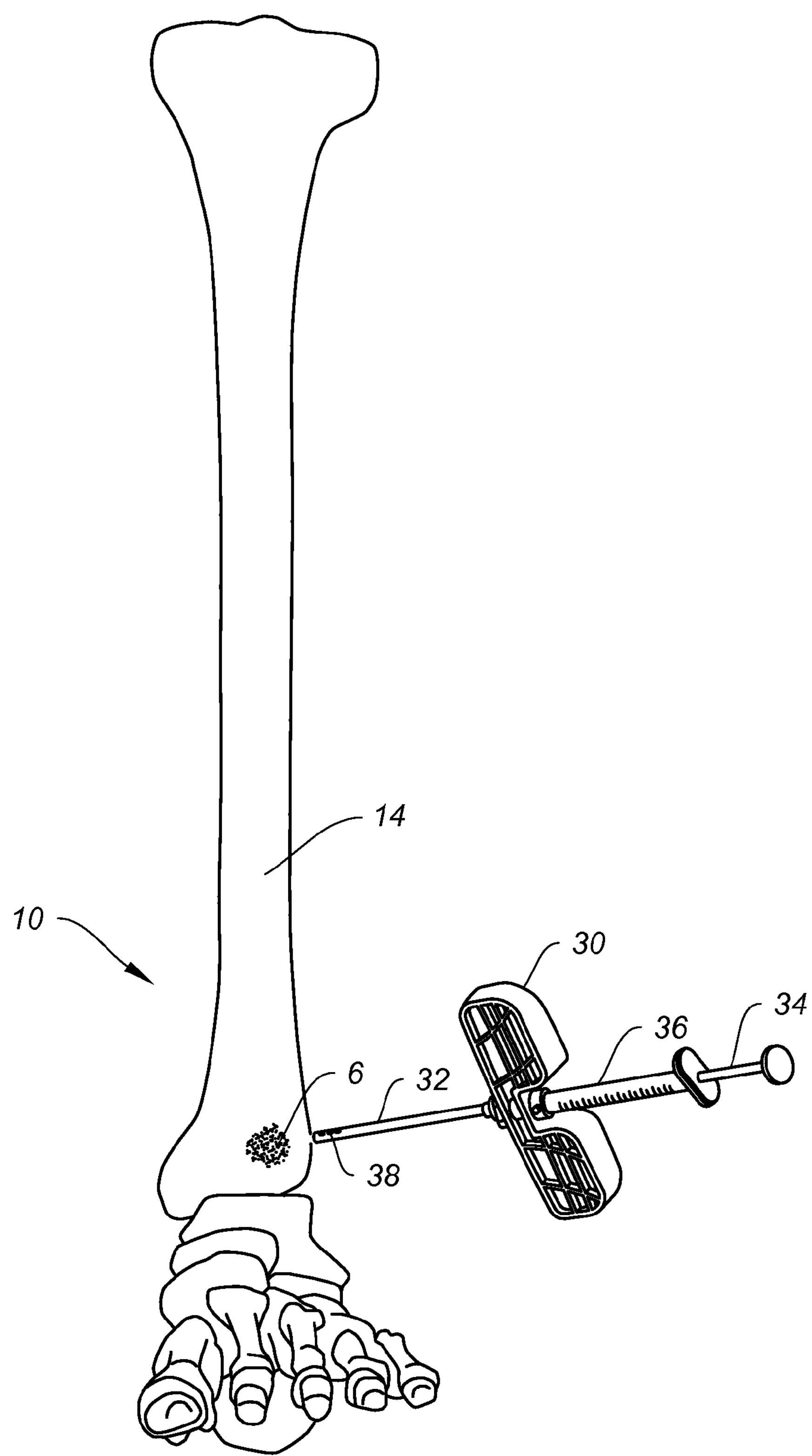

FIGS. 41-44 illustrate exemplary methods of treating a subchondral defect of an ankle joint 10 in accordance with the present disclosure. As previously discussed, one manner of treating pain associated with osteoarthritis of the ankle joint 10 is to identify and stabilize a subchondral defect in the bone of the small joint. Using any one of the guide or access instruments described herein, a surgeon may place a pin 2 into a location at or near the subchondral defect of the bone, such as the talus 12 of FIG. 41. A cannula 32 may be slid over the pin 2, and the pin 2 removed to leave the cannula 32. Then, an injection system comprising a syringe 36, plunger 34 with associated handle 30 may be applied to the cannula 32, as shown generally in FIGS. 41-44. The syringe 36 may include a bone hardening material, such as a bone substitute material or other material as described above. The material may be injected through the cannula 32 and through its ports 38 at its distal end, as shown in FIGS. 43 and 44, leaving the material inside the subchondral region of the bone to stabilize the targeted defect.

As further illustrated, the exemplary treatment methods may be performed by targeting different access points at or near the small joint. For example, FIG. 41 shows treatment through access to the talus bone 12, while FIG. 42 shows treatment through access to the calcaneous bone. FIGS. 43 and 44 show treatment through the tibia bone 14. Again, similar to a knee joint where either or both of the tibial and femur can be targeted for subchondral treatment, the distal tibia and/or the talus or calcaneous bone may be targeted in ankle joint treatment.

Finally, the treatments and instruments of the present disclosure may be applied to other small joints like the wrist, elbow, or even shoulder joint, in a similar manner as described and illustrated herein for an ankle joint.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A guide instrument system for delivering an instrument to a subchondral region of a talus bone of an ankle joint, the guide instrument comprising:

a guide frame comprising a notched tab and also providing at least a first guide frame opening in the guide frame for receiving a fixation element through the first guide frame opening for fixing the guide frame to a tibia bone of the ankle joint;

an alignment bar including a first notched arm that is receivable in the notched tab of the guide frame for detachably connecting the alignment bar to the guide frame to form a tibial fixation assembly for aligning the guide frame relative to an anatomical landmark associated with the ankle joint, wherein the alignment bar, when detachably connected to the guide frame with the guide frame fixed to the tibia bone, is detachable from the guide frame while the guide frame remains fixed to the tibia bone; and a guide ring including a second notched arm that also is detachably receivable in the notched tab of the guide frame but non-concurrently with the first notched arm of the alignment bar such that the alignment bar and the guide ring are interchangeably connectable to the guide frame, the guide ring providing a plurality of guide ring openings in the guide ring for receiving an instrument or tool through the guide ring openings for guiding the instrument or tool to the subchondral region of the talus bone of the ankle joint, wherein each of said guide ring openings provides a predefined trajectory path into the subchondral region of the talus bone of the ankle joint, a plurality of the trajectory paths intersecting at a focal point.

2. The guide instrument system of claim 1, wherein the anatomical landmark is the dome of the talus bone.

3. The guide instrument system of claim 1, wherein the fixation element comprises a fixation pin.

4. The guide instrument system of claim 1, wherein the guide frame provides a plurality of guide frame openings.

5. The guide instrument system of claim 4, wherein one of the plurality of guide frame openings is configured as an elongate slot.

* * * * *